United States Patent [19]

Passafaro et al.

[11] Patent Number: 6,156,046

[45] Date of Patent: Dec. 5, 2000

[54] METHODS AND SYSTEMS FOR TREATING OBSTRUCTIONS IN A BODY LUMEN

[75] Inventors: James D. Passafaro, Los Gatos; Ronald G. Williams, Menlo Park; David J. Kupiecki, San Francisco; Greg R. Patterson, Pleasanton; Kathy M. Mah, Mountain View, all of Calif.

[73] Assignee: Prolifix Medical, Inc., Sunnyvale, Calif.

[21] Appl. No.: 08/966,001

[22] Filed: Nov. 7, 1997

[51] Int. Cl.[7] .................................................. A61B 17/22
[52] U.S. Cl. ............................................. 606/159; 128/898
[58] Field of Search .................................... 606/159, 170, 606/171, 176, 180; 128/898

[56] References Cited

U.S. PATENT DOCUMENTS

| | | | |
|---|---|---|---|
| 5,143,085 | 9/1992 | Wilson | 128/772 |
| 5,632,755 | 5/1997 | Nordgren et al. | 606/159 |
| 5,876,414 | 3/1999 | Straub | 606/159 |
| 5,879,361 | 3/1999 | Nash | 606/159 |

*Primary Examiner*—Michael Buiz
*Assistant Examiner*—Kevin Truong
*Attorney, Agent, or Firm*—Townsend and Townsend and Crew LLP

[57] ABSTRACT

A system is provided having a catheter, a torque member extending longitudinally through a lumen of the catheter, a removal mechanism secured to a distal end of the torque member, and a guidewire having a guide section that extends through a lumen of the removal mechanism. The guide section defines a curved profile that is diametrically larger than the dimension of the removal mechanism. The guide section of the guidewire is adapted to be positioned inside a passageway of the occluding material, and provides a curved path along which the removal mechanism can be advanced inside the passageway of the occluding material to separate and remove occluding material.

29 Claims, 19 Drawing Sheets

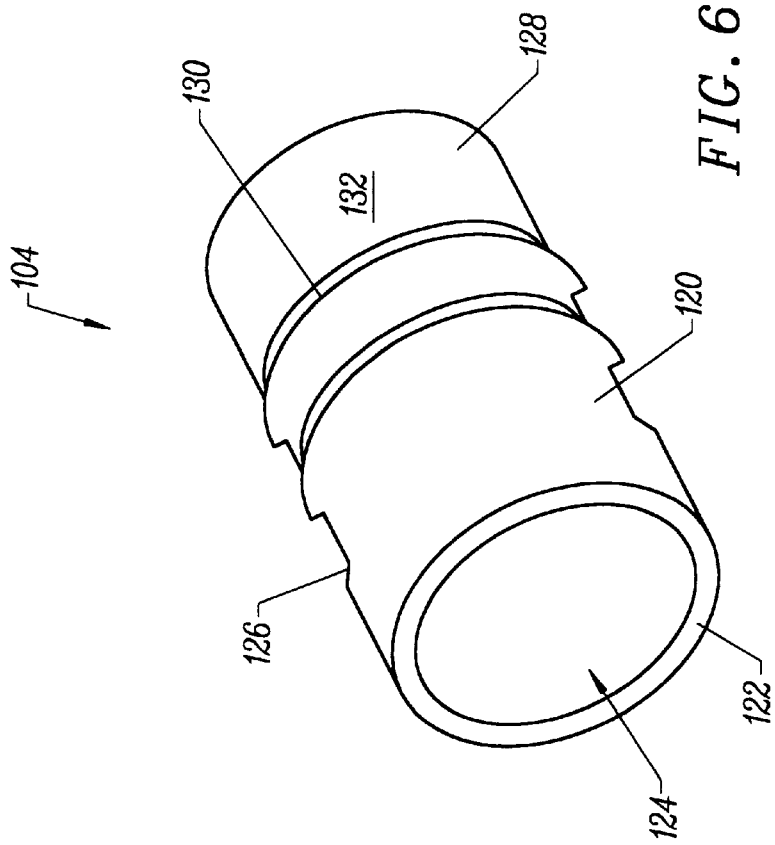
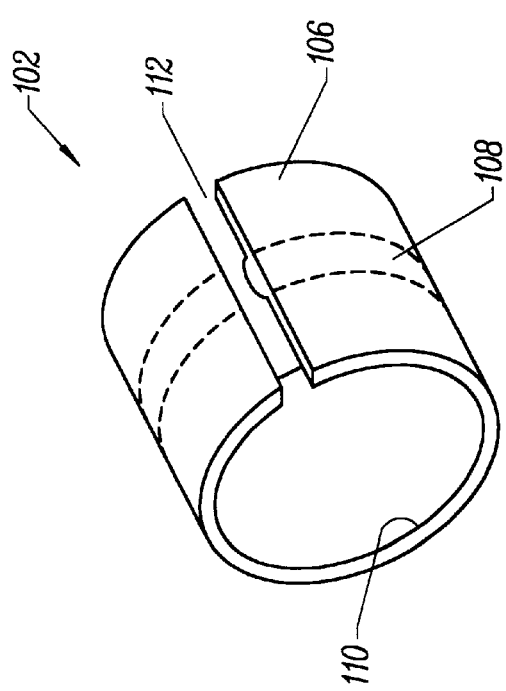

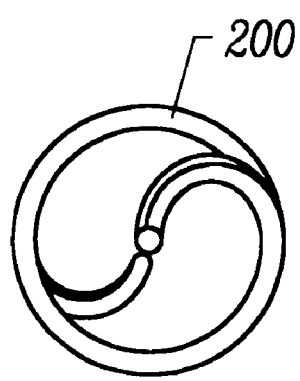 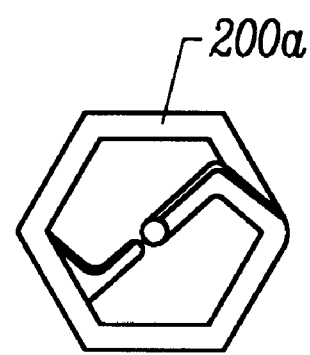
*FIG. 8A*  *FIG. 8D*

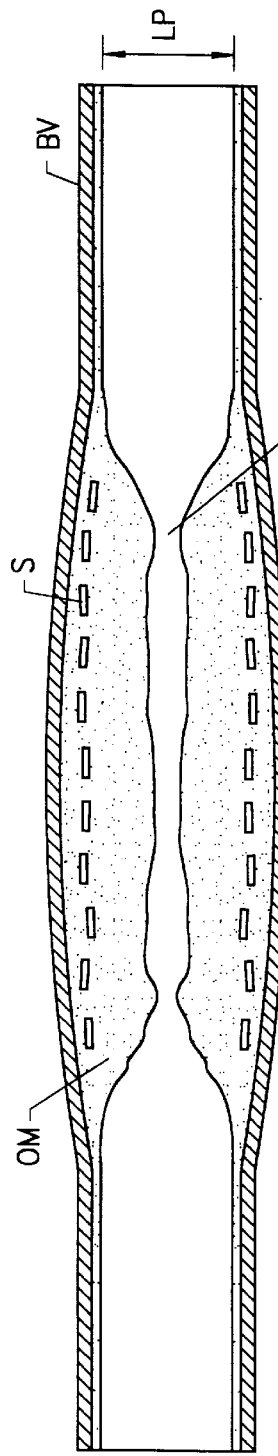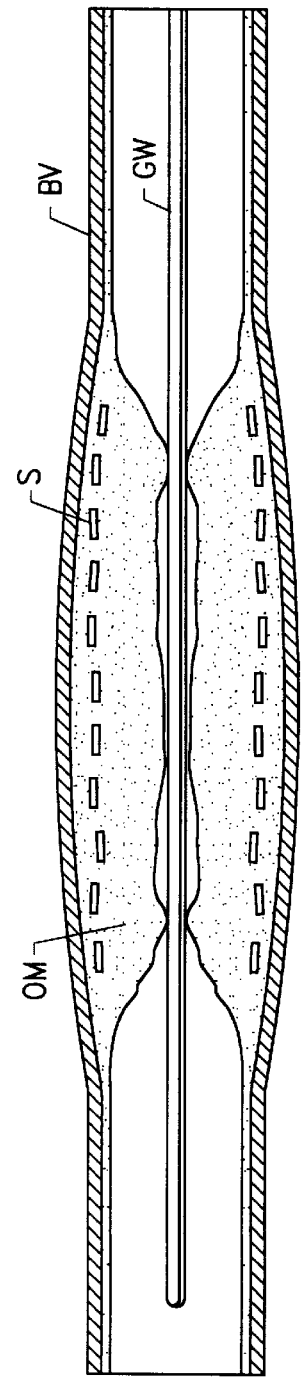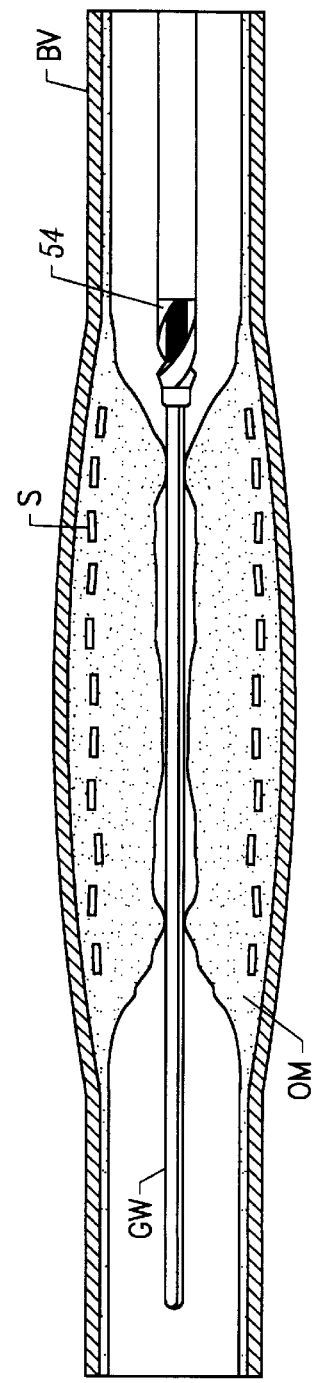

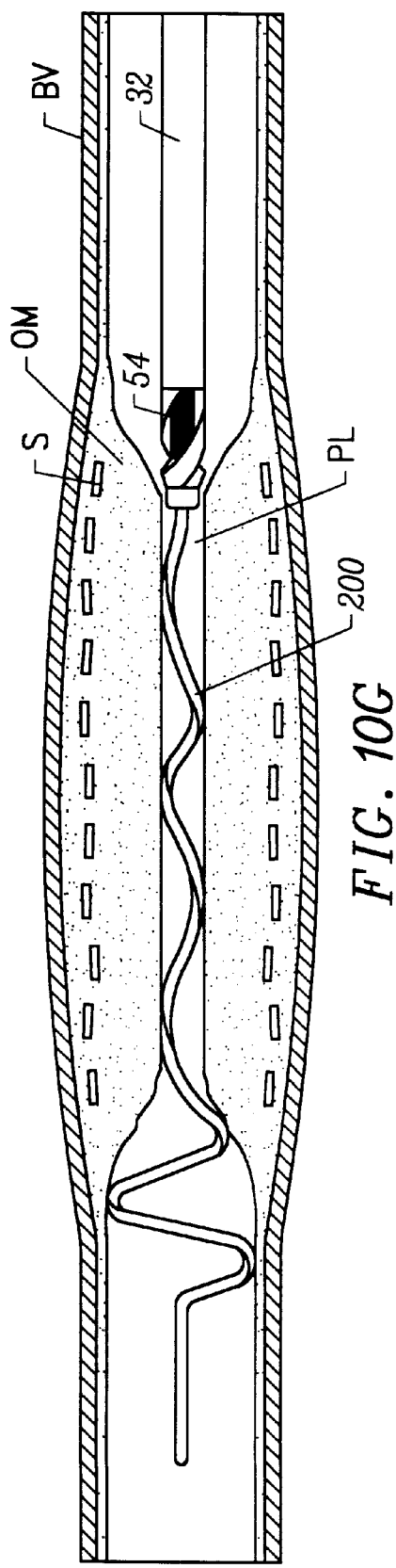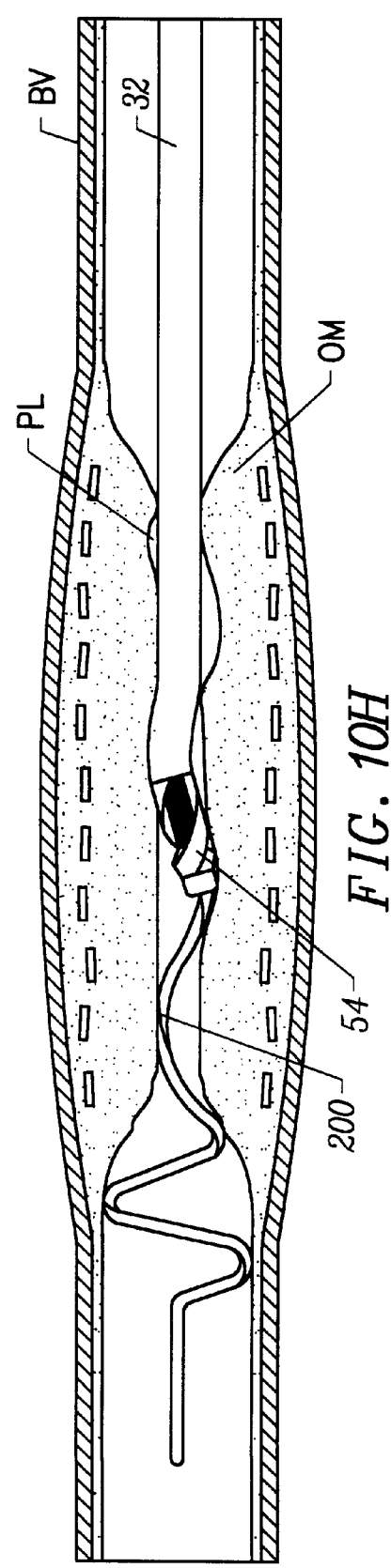
FIG. 10G
FIG. 10H

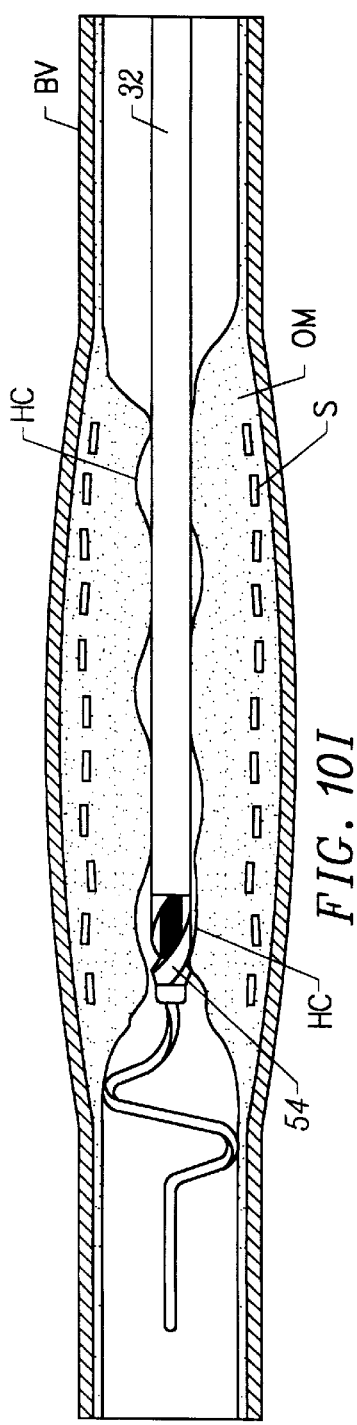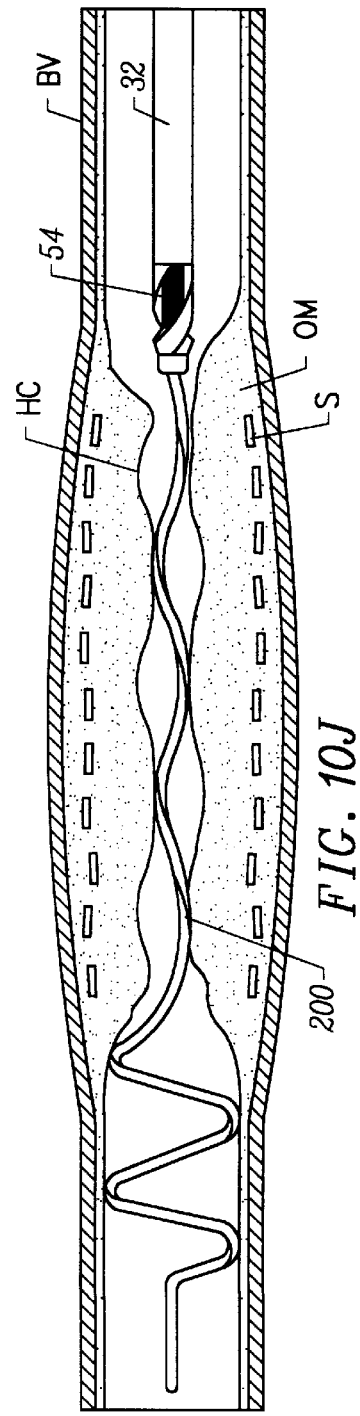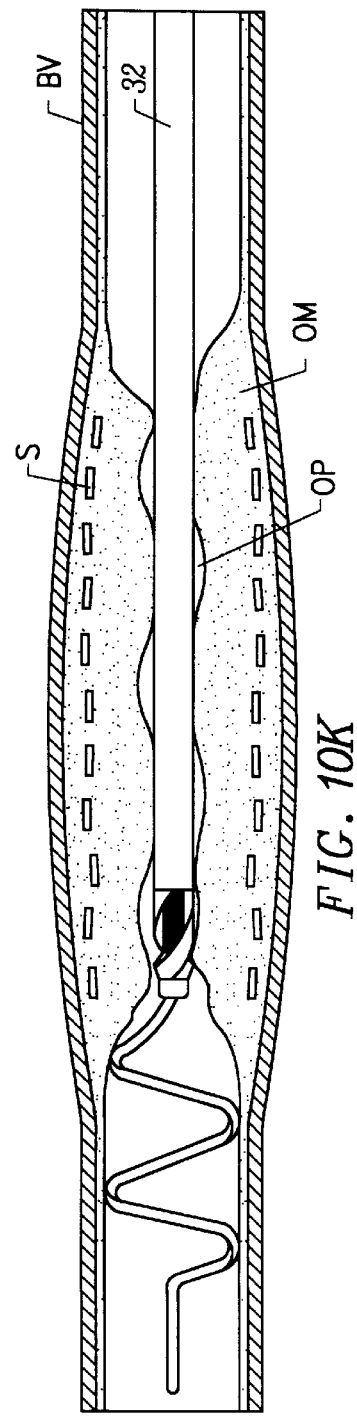

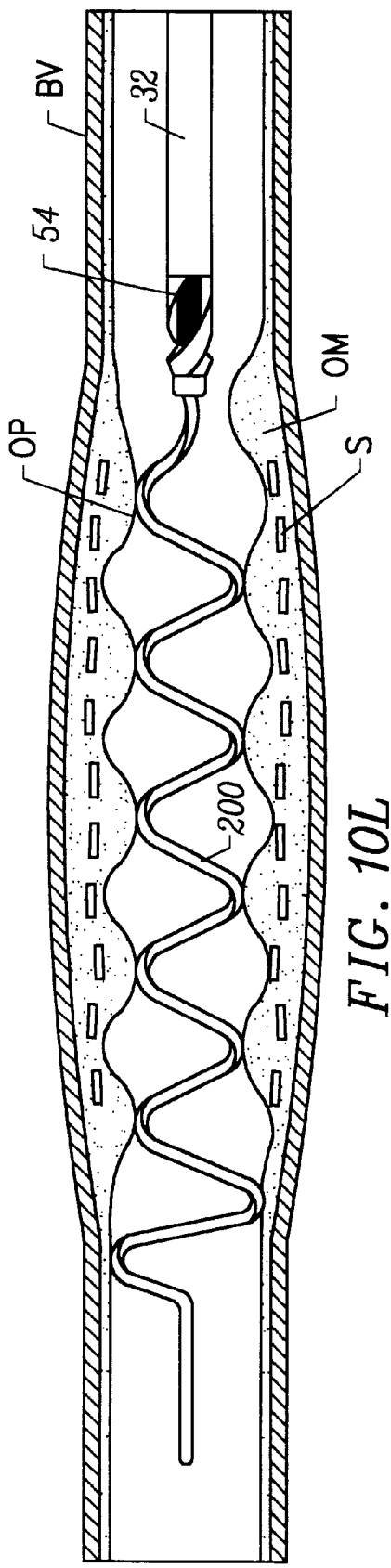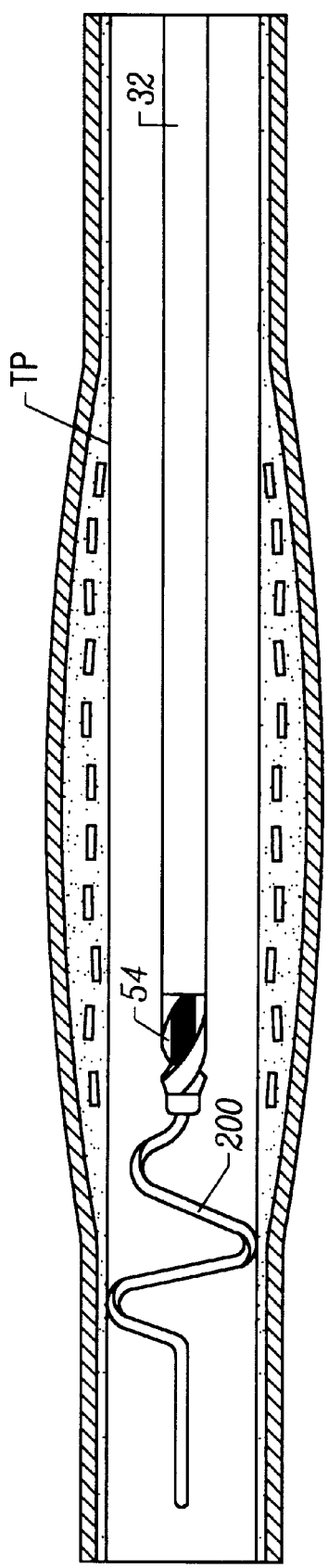

METHODS AND SYSTEMS FOR TREATING OBSTRUCTIONS IN A BODY LUMEN

BACKGROUND OF THE INVENTION

1. Field of the Invention

The present invention relates generally to apparatus and methods for treating and removing occluding material from a body lumen, such as blood vessels. In particular, the present invention relates to apparatus and methods for guided atherectomy.

2. Description of the Prior Art

A number of methods and devices are currently available for removing stenotic or occluding material from a blood vessel, and for restoring adequate blood flow to the blood vessel. One common procedure is known as percutaneous transluminal angioplasty (PTA), in which a catheter that is provided with a dilatation balloon at its distal end is positioned in a blood vessel at the site of the stenosis. The balloon is then expanded to dilate the blood vessel in order to restore adequate blood flow to regions beyond the stenosis.

While often effective PTA suffers from certain limitations. For example, PTA can be effective only if the occluding material in the blood vessel has a sufficiently large opening to allow the balloon to be positioned inside the occluding material. Where the blood vessel is almost completely occluded, it is difficult if not impossible to position the balloon of a catheter inside the occluding material. In addition, PTA suffers from multiple intra-procedural and post-procedural problems: abrupt closure, elastic recoil, and restenosis. Abrupt closure is the rapid reocclusion of the blood vessel within hours of the initial treatment. Abrupt closure can result from rapid thrombus formation which occurs in response to injury of the vessel wall from the PTA procedure. Elastic recoil is the elastic recovery of the dilated vessel approaching its pre-procedural diameter. Restenosis is the re-narrowing of the blood vessel over the weeks or months following an initial apparently successful PTA procedure. Restenosis occurs in up to 50% of all PTA patients and results from smooth muscle cell proliferation and migration and remodeling.

To overcome these limitations, a variety of catheters and techniques have been proposed which employ a removal mechanism to separate and remove occluding material from the luminal wall of the blood vessel. For example, rotational atherectomy devices (e.g., the Transluminal Extraction Catheter made by Interventional Technologies of San Diego, Calif., and the Rotablator, made by Boston Scientific of Bellevue, Wash.) rely on a rotating removal mechanism that can be advanced axially through vessels that are almost entirely occluded. The mechanisms, however, are available only in predetermined sizes, such as predetermined outer diameters. As a result, these removal mechanisms are most effective when used in blood vessels having a lumen size that approximate the size of the removal mechanism. These removal mechanisms are difficult to use in smaller-diameter blood vessels, and are less effective in removing occluding material from blood vessels having lumen sizes larger than the size of the removal mechanisms. This is a significant limitation since the lumen size, the size and extent of the occluding material, and the location of the occluding material, will vary widely for different patients.

To address this problem, many currently-available devices (e.g., the Simpson Atherocath® atherectomy catheter made by Guidant Corporation of Santa Clara, Calif., and the Redha-Cut, made by Sherine Med of Utzenstorf, Switzerland) are provided with eccentrically displaceable or radially expandable removal mechanisms respectively. These removal mechanisms are introduced into the blood vessel in a collapsed or compressed state inside a sheath or delivery catheter, and are then radially expanded or eccentrically displaced (e.g., displaced eccentrically by a balloon) at the site of the occluding material to separate and remove the occluding material. Unfortunately, the buildup and formation of the occluding material is rarely consistent since more occluding material may have formed at one location than at another location in the stenosed or occluded region of the blood vessel. Since the radially expandable removal mechanisms are typically expanded by the same radial distance throughout, the removal mechanism will remove material at a generally equal rate in all radial directions and may not be effective in removing all of the occluding material at locations where there has been a greater build-up of occluding material. If the procedure is continued until all material is removed, the removal mechanism may damage the vessel wall at locations where there was less build-up of occluding material.

In contrast, the eccentrically displaceable removal mechanisms can remove asymmetric build-ups of occluding material, but rely on the ability of the physician to orient the cutting window towards the occluding material, which may be at varying discrete locations along the length of the stenosis. Moreover, because they remove material in an asymmetric manner, if proper care is not exercised in their expansion, orientation and use, directional atherectomy devices can injure the luminal wall of the blood vessel (e.g. shaped wire multi-burr Rotational Ablation Device, U.S. Pat. No. 5,584,843, and the Abrasive Drive Shaft Device for Directional Rotation Atherectomy, U.S. Pat. No. 5,360,432). Thus, neither radially expandable nor eccentrically displaceable removal mechanisms are sufficiently capable of effectively adapting to the specific nature of the lumen and the occluding material.

The problems associated with proper sizing of the device, the nature and size of the occluding material, and the location of the occluding material are further magnified when treating stented regions of blood vessels that have restenosed. To address the problems of abrupt closure, elastic recoil, and restenosis described above, PTA procedures have been followed by implanting vascular stents inside the blood vessel at the treatment site. These stents are thin-walled scaffolds which are expanded at the treatment site to act as a mechanical support for the luminal wall of the blood vessel, thereby inhibiting elastic recoil. Although the stent diminishes the contribution of remodeling to vessel narrowing, restenosis still occurs frequently at the stented regions of blood vessels. This is because most stents comprise an open lattice, and cell proliferation (often referred to as hyperplasia) can occur in the interstices between the support elements of the lattice. As a result, instead of forming a barrier to hyperplasia and restenosis, the stent can become embedded within an accumulated mass of thrombus and tissue, and the treatment site becomes stenosed again. Treatment of an occluded stent faces all the difficulties discussed above with respect to treatment of initial occlusions and is further complicated by the need to avoid damaging the stent during the removal of the hyperplasia occluding material.

Thus, there remains a need for improved methods and apparatus for treating and removing occluding material from a blood vessel. In particular, it would be desirable to provide apparatus and methods which can remove material from vessels which are almost fully occluded, which can treat vessels having a range of sizes, and which can conform to a particular vessel size and lumenal shape during the course of a procedure. In addition, the apparatus and methods of the present invention should be effective for use in removing occluding material that engulfs an implanted stent. Desirably, the apparatus and methods of the present invention will be easy to implement, present acceptable risks to the patient, and be readily performed by physicians who are familiar with balloon angioplasty and other conventional intravascular treatments. At least some of these objectives will be met by the embodiments of the present invention described below.

SUMMARY OF THE INVENTION

A system according to the present invention comprises a catheter, a torque member extending longitudinally through a lumen of the catheter, a removal mechanism secured to a distal end of the torque member, and a guidewire having a guide section which defines a curved profile that is diametrically larger than the dimension of the removal mechanism. The guide section of the guidewire is adapted to be positioned inside a passageway of the occluding material, and provides a curved path along which the removal mechanism can be advanced inside the passageway of the occluding material to separate and remove occluding material.

In the system of the present invention, the torque member is usually rotationally driven by a driver, typically a hand-held device. The driver houses a motor which rotates a proximal end of the torque member, thereby causing the removal mechanism to rotate. The removal mechanism can be any rotational atherectomy device, e.g. a rotatable helical cutter, a rotatable modified Forstner cutter, a rotary cutting burr, a sidecutter having a housing with a rotatable cutting window, or any other similar device that can be used to separate and remove occluding material from the wall of the body lumen. A bearing assembly is usually provided to allow rotation of the removal mechanism and the torque member, while preventing axial movement of the torque member and removal mechanism relative to the catheter.

The system of the present invention may further include a conveyor mechanism which is used to convey separated occluding material to a collection reservoir that is coupled to the proximal end of the catheter. The conveyor mechanism may be provided in the form of a "screw-pump" arrangement, e.g. an outer coil on the torque member within the lumen of the catheter. Alternatively or additionally, the conveyor mechanism may comprise a vacuum source connected to the proximal end of the catheter to draw material back through the lumen thereof. Alternatively or additionally, the conveyor mechanism may comprise a plurality of propellers or impellers.

According to one non-limiting aspect of the present invention, the guide section of the guidewire is configured to exert a radial outward force against a luminal wall of a vessel into which it is positioned. In one embodiment, the guide section of the guidewire has a three-dimensional helical configuration which brings the removal mechanism in apposition with the occluding material of the stenosed portion of the luminal wall so that the removal mechanism can separate and remove the occluding material. The guide section of the guidewire will preferably assume a generally straightened configuration while in the lumen of the torque member. The guidewire can be provided with a generally straight proximal section extending proximally from the guide section, and a generally straight distal section extending distally from the guide section, with the distal and proximal sections of the guidewire extending along the same longitudinal axis.

Methods of the present invention create a series of diametrically larger passageways in the occluding material, until a passageway having the desired diameter has been obtained. A removal mechanism is advanced over a guide section of a guidewire to separate and remove occluding material and create curved channels or grooves in the occluding material. The removal mechanism may be repeatedly advanced and partially withdrawn over the guide section with optional periodic axial translation of the guide section of the guidewire within the passageway of the occluding material. By thus removing successive confluent channels of occluding material, a second passageway that is diametrically larger than the initial passageway is created.

Optionally, the width or diameter of the guide section of the guidewire can be increased to enhance the removal. For example, the existing guidewire can be exchanged for another guidewire having a diametrically larger guide section. Alternatively, shape memory alloy guidewires can be heated (or cooled) or otherwise have energy applied to effect a further shape change. The removal mechanism is then advanced over the larger guide section of the new guidewire to create a third passageway that is diametrically larger than the second passageway. This process can be repeated to create progressively larger passageways, until a passageway having the desired diameter is obtained.

In a particular aspect of the apparatus of the present invention, the apparatus comprises a catheter and a guidewire. The catheter includes a catheter body having a proximal end, a distal end, and a lumen therethrough. A removal mechanism disposed at the distal end of the catheter body and arranged to excise material from a body lumen and direct the excised material into the lumen of the catheter. The removal mechanism will follow a curved path, usually comprising at least one cutting guide which excises material by forwardly advancing the blade into the material and forming a clear separation between two portions of the material. Such cutting mechanisms will not comprise abrasive surfaces of the type which may be employed in other aspects of the present invention. The guidewire will define a curved path, preferably a helical path, where the catheter body can be advanced over the guidewire to deflect the cutting mechanism over such curved path. Preferably, the cutting mechanism will have a width which is no more than 1.2 times the width of the catheter body at its distal end, preferably being equal to or of a lesser diameter than said distal end. More preferably, the cutting blade will comprise a helical blade or blade assembly which is attached to the distal end of the torque member disposed within the lumen of the catheter. The helical blade will preferably have a diameter no greater than that of the diameter of the catheter body at its distal end. An exemplary and preferred helical blade assembly comprises a pair of blades arranged as a double helix and tapered to a reduced diameter toward a distal end thereof.

In yet another aspect of apparatus of the present invention, a system comprises a catheter and a guidewire, where the guidewire may be the same as that described immediately above. The catheter will comprise a catheter body having a proximal end, a distal end, and a lumen therethrough. A helical blade will be disposed at the distal end of the catheter body, and the catheter will preferably comprise a torque member disposed within the lumen of the catheter body. The helical blade will preferably have the structures described immediately above.

In still another aspect of the apparatus of the present invention, an atherectomy catheter comprises a catheter body, a torque member, and a helical blade. As used herein, "atherectomy" is intended to refer to the removal of hyperplasia material following angioplasty and/or stenting as well as the removal of atheroma (from which the name is derived). The catheter body has a proximal end, a distal end, and a lumen therethrough. The torque member also has a proximal end, a distal end, and a lumen therethrough, and the torque member is rotatably disposed in the catheter body lumen. An annular lumen is defined between the exterior surface of the torque member and the interior surface of the catheter body lumen, and a helical blade assembly is attached to the distal end of the torque member. The helical blade assembly comprises at least one helical blade which is tapered in the distal direction and which has an interior which is open to the annular lumen of the catheter body. In this way, the helical blade can be advanced through occluding material to excise that material and direct it into the annular lumen for collection and optionally disposal. Preferably, the helical blade assembly comprises at least two helical blades disposed as a double helix, i.e. in parallel to each other. In a still further preferred aspect, a helical screw may be formed over at least a distal portion of the torque member. In this way, as the torque member is rotated, the helical screw can act as an "Archimedes" screw pump to facilitate removal of excised material. Usually, the atherectomy catheter will further comprise a port or other means in fluid communication with the annular lumen for applying a vacuum to remove excised material through the annular lumen, either by itself or in combination with rotation of the helical screw pump, pump impellers, or other mechanisms.

In a specific aspect of the method of the present invention, a region of occluded material in a body lumen is treated by positioning a guidewire having at least one curve within the region of occluding material. The curve on the guidewire resiliently engages a peripheral portion of the region within the occluding material, and a cutting blade is advanced over the guidewire to excise occluding material from the lumen in order to enlarge said lumen. Preferably, the guidewire will be initially advanced in a straight configuration into the region. Thereafter, the straight guidewire will be allowed or induced to assume a geometry having at least one curve. For example, the guidewire may be heated to induce a phase change causing the guidewire to assume a helical configuration. Preferably, the guidewire will be constrained within a catheter, sheath, or other constrained body, and released at a target site to assure an unconstrained or partially constrained diameter within the body lumen. Further preferably, advancing the cutting blade will comprise rotating a helical blade as it is axially advanced over the guidewire. The method may further comprise collecting excised material from an interior volume within the helical blade and removing the collected material from the body lumen.

In another specific aspect of the method of the present invention, the region of occluding material in a body lumen is treated by introducing a guidewire through the region. The guidewire is then heated to induce at least one curve in the guidewire. A removal mechanism, such as a cutting blade, is then advanced over the guidewire, and the curve engages or deflects the removal mechanism against a peripheral portion of the region as the removal mechanism is advanced. Usually the guidewire is a shape memory alloy. Alternatively, the guidewire is a heat memory alloy where the heating step induces a phase change from martensitic to austenitic, wherein the austenitic phase has a curved memory. More preferably, the curve is a helix. Advancing of the removal mechanism generally comprises rotating a cutting blade, more usually where the cutting blade is a tapered helical cutting blade or cutting assembly.

In a still further aspect of method of the present invention, hyperplastic material may be removed from the interior of a stent within an artery by positioning a helical guidewire within the stented region of the artery. A removal mechanism, which can be any of the mechanisms described above, is then advanced over the guidewire to create a helical channel in the hyperplastic material. The removal mechanism is repeatedly advanced over the guidewire for a number of times sufficient to expose at least a portion of the stent to substantially all the hyperplastic material from within the lumen of the stent. Positioning of the guidewire preferably comprises advancing a straight guidewire into the stented region and thereafter inducing the helical geometry therein e.g. by heating the guidewire to induce a phase change. Advancing of the removal mechanism usually comprises rotating a cutting blade, more usually rotating a helical cutting blade having a tapered distal end. The removal step is usually repeated at least 2 times, preferably at least 3 times, more preferably at least 4 times, often at least 8 times, sometimes at least 12 times, and as many as 20 times or more in order to achieve the substantially complete removal of the hyperplastic material from within the stent.

BRIEF DESCRIPTION OF THE DRAWINGS

FIG. 5 is a perspective view of a snap ring of a bearing assembly that can be used with the system of FIG. 1.

FIG. 6 is a perspective view of a shell of a bearing assembly that can be used with the snap ring of FIG. 5, and with the system of FIG. 1.

FIG. 8A is a cross-sectional view of the distal end of the guidewire of FIG. 8.

FIG. 8D is a cross-sectional view of the distal end of another guidewire based on the principles of the guidewire of FIG. 8.

FIGS. 10A–10M illustrate one method of using the system of FIG. 1 for treating and removing occluding material from a blood vessel.

DESCRIPTION OF THE PREFERRED EMBODIMENT

Figures 1, 1A:
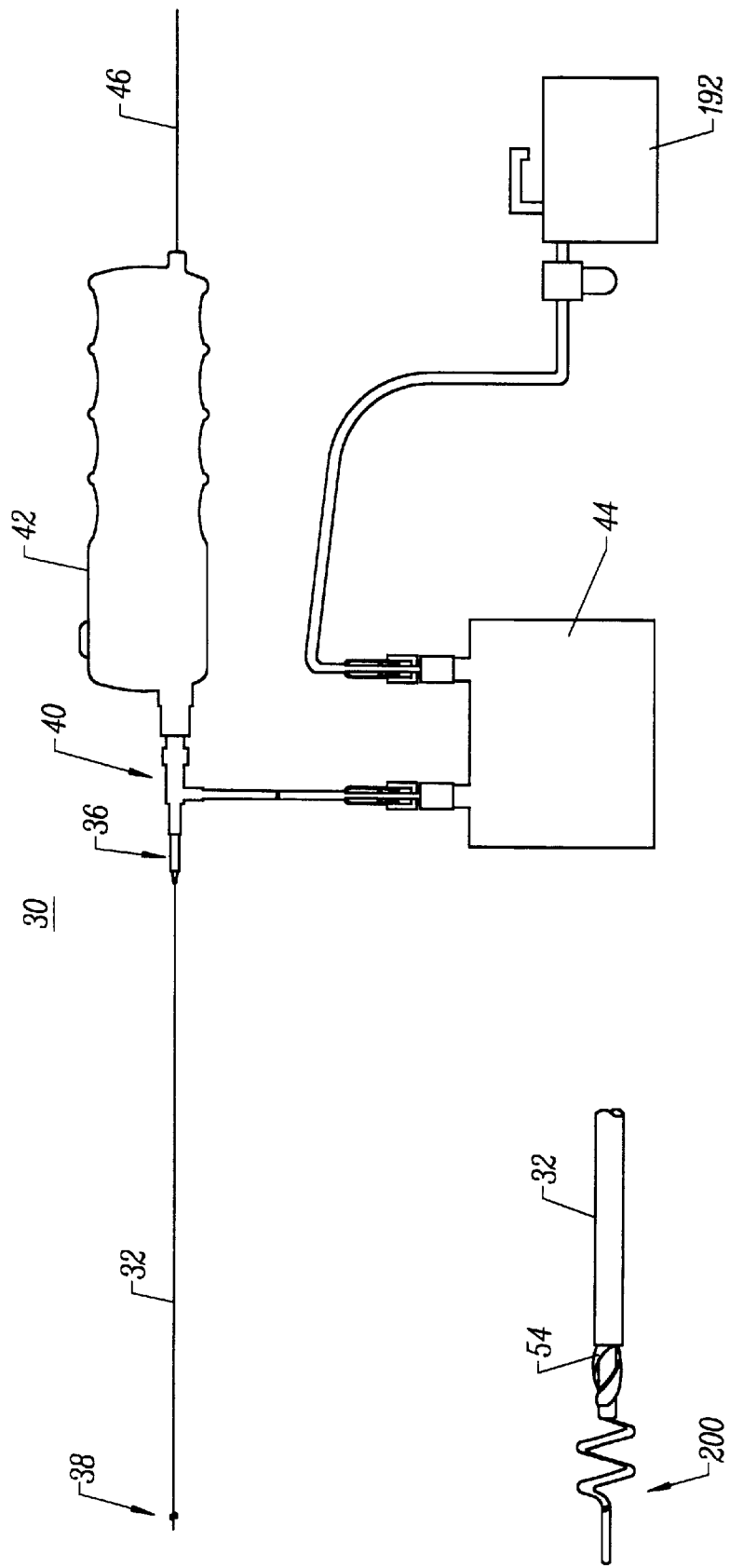
FIG. 1 illustrates a system according to the present invention.
FIG. 1A is a detail view of the distal end of the catheter and guidewire of the system of FIG. 1.

The following detailed descriptions are the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention provides apparatus and methods for use in treating and removing occluding material from a blood vessel or other body lumen of an animal or human. The system provides a removal mechanism that is secured at a distal end of a torque member. The torque member extends through a catheter that is used to carry and deliver the removal mechanism to the site of the occluding material inside the vessel, where the removal mechanism is actuated to separate and remove occluding material. A guidewire is used to guide the removal mechanism in a controlled manner at and along the location of the occluding material to separate and remove portions of the occluding material. In particular, the guidewire is provided with a helical distal guide section that guides the removal mechanism along the luminal wall to separate and remove the occluding material. The helical section of the guidewire may have an unconstrained diameter that is larger than the outer diameter or size of the removal mechanism. Passage of the removal mechanism over the deployed guidewire will remove one layer of occluding material to produce a diametrically larger passageway in the occluding material. The helical guide section of the guidewire may be increased in size and/or exchanged with a guidewire having a larger helical diameter to remove additional layers of occluding material to provide diametrically larger passageways of the occluding material.

As used herein, "occluding material" means any proliferative or anomalous tissues or substances that occupy a lumen and represent a blockage that impedes the lumen's normal function. "Occluding material" can include, but is not limited to, such materials as thrombus, emboli, atheroma, smooth muscle cell hyperplasia, and other proliferative or anomalous tissues.

As used herein, "superelastic" refers to the property of a material, usually a metal alloy, which permits the material to return to its original shape upon unloading after a substantial deformation. Superelastic alloys can be strained up to ten times more than ordinary spring materials without being plastically deformed. The elasticity exhibited is unusually large and is caused by a stress induced phase transformation (i.e. austenite to martensite or stress induced martensite).

As used herein, "elastic and "resilient" refer to the property of a material to return to its original shape after unloading. The elastic properties of most materials are limited by plastic deformation which occurs at a relatively low degree of strain. Some materials, such as spring stainless steels, will posses sufficient elasticity for at least some applications within the present invention.

As used herein, "shape memory material" refers to those materials, usually metal alloys, which return to an original shape (which may be "set" during fabrication of the material) after heating above and/or within a characteristic temperature range (i.e. $A_s$-$A_f$). If a straight piece of wire in the austenitic condition is cooled below and/or within a characteristic temperature range (i.e. $M_s$-$M_f$) to form martensite it remains straight. If the twinned martensite is deformed by bending it is converted to deformed martensite. On heating the transformation back to austenite occurs and the wire becomes straight again.

Some materials, such as certain nickel titanium alloys, e.g. Nitinol®, display both superelastic and shape memory properties and thus may be used according to more than one aspect of the present invention as described below in more detail.

Figure 2:
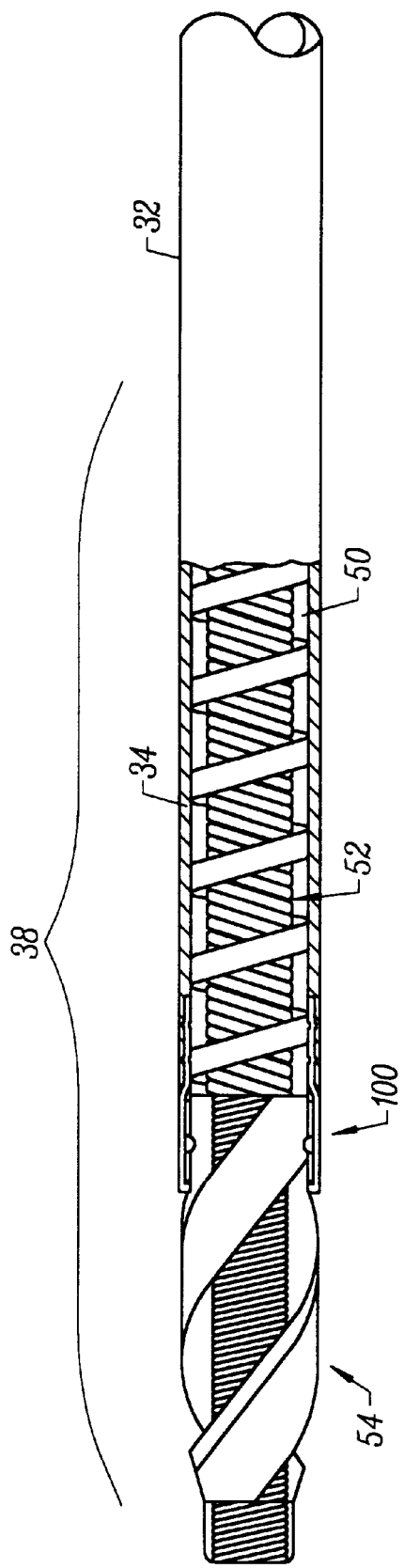
FIG. 2 is an enlarged broken-out view of the distal end of a catheter and removal mechanism that can be used with the system of FIG. 1.

FIGS. 1, 1A and 2 illustrate a system 30 according to the present invention. The system 30 includes a catheter 32 which has a flexible elongate catheter body 34 having a proximal end 36 and a distal end 38, and defining at least one lumen 50 extending longitudinally therethrough. The catheter 32 is operatively coupled, by way of a proximal connector assembly 40, to a hand-held device 42 and a collection reservoir 44. The hand-held device 42 includes a motor for rotating a removal mechanism 54 provided at the distal end 38 of the catheter 32 to separate, remove and extract occluding material, as described in greater detail hereinbelow. The collection reservoir 44 collects occluding material that has been removed and extracted from the blood vessel. A guidewire 46 extends through, and is used in conjunction with, the catheter 32, as will be more fully described below.

Figure 3:
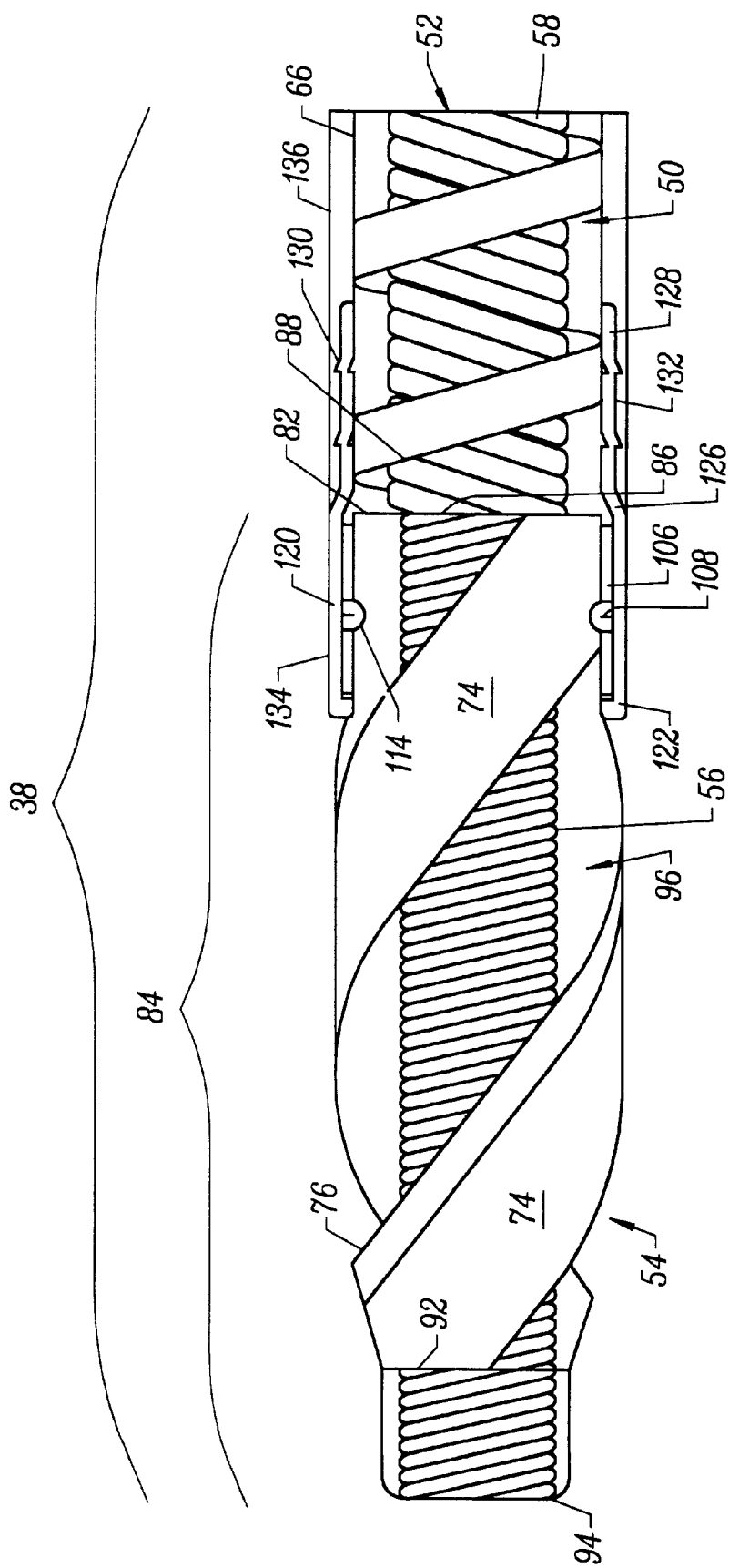
FIG. 3 is a sectional view of the distal end of the catheter and removal mechanism of FIG. 2.

Referring to FIGS. 2 and 3, the catheter body 34 of the catheter 32 is preferably composed of a flexible polymer material that is biocompatible, kink resistant, and lubricious. Desirable polymer materials can include polyethylenes, polyurethanes, polyamides, fluoropolymers or the like. The flexible catheter body 34 is preferably in the form of an elongate tube having one lumen 50 extending longitudinally therethrough. Optionally, the catheter body 34 may be reinforced with a plurality of braids, helices, axial filaments, and the like, although the exemplary embodiment is free of such reinforcement. The tube may also be composed of composites and mixtures of more than one polymeric material. Extending longitudinally through the lumen 50 of the catheter body 34 is an elongate torque member 52 having a proximal end 64 (see FIG. 7) which is connectable to the hand-held device 42 for translating rotational motion from the hand-held device 42 to the removal mechanism 54 that is secured to its distal end.

1. The Torque Member 52

Figure 4:
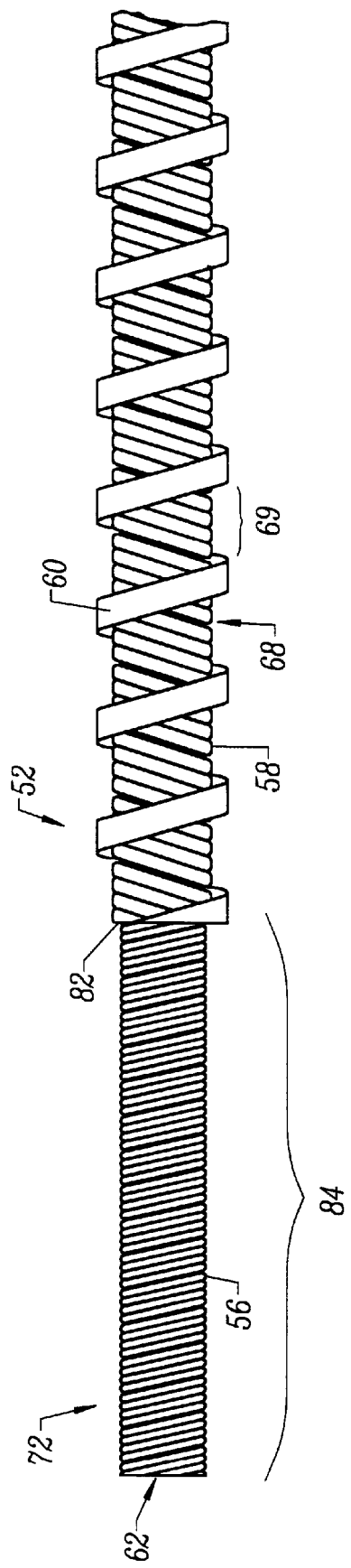
FIG. 4 is a partial cut-away side view of a torque member that can be used with the system of FIG. 1.
Figure 7:
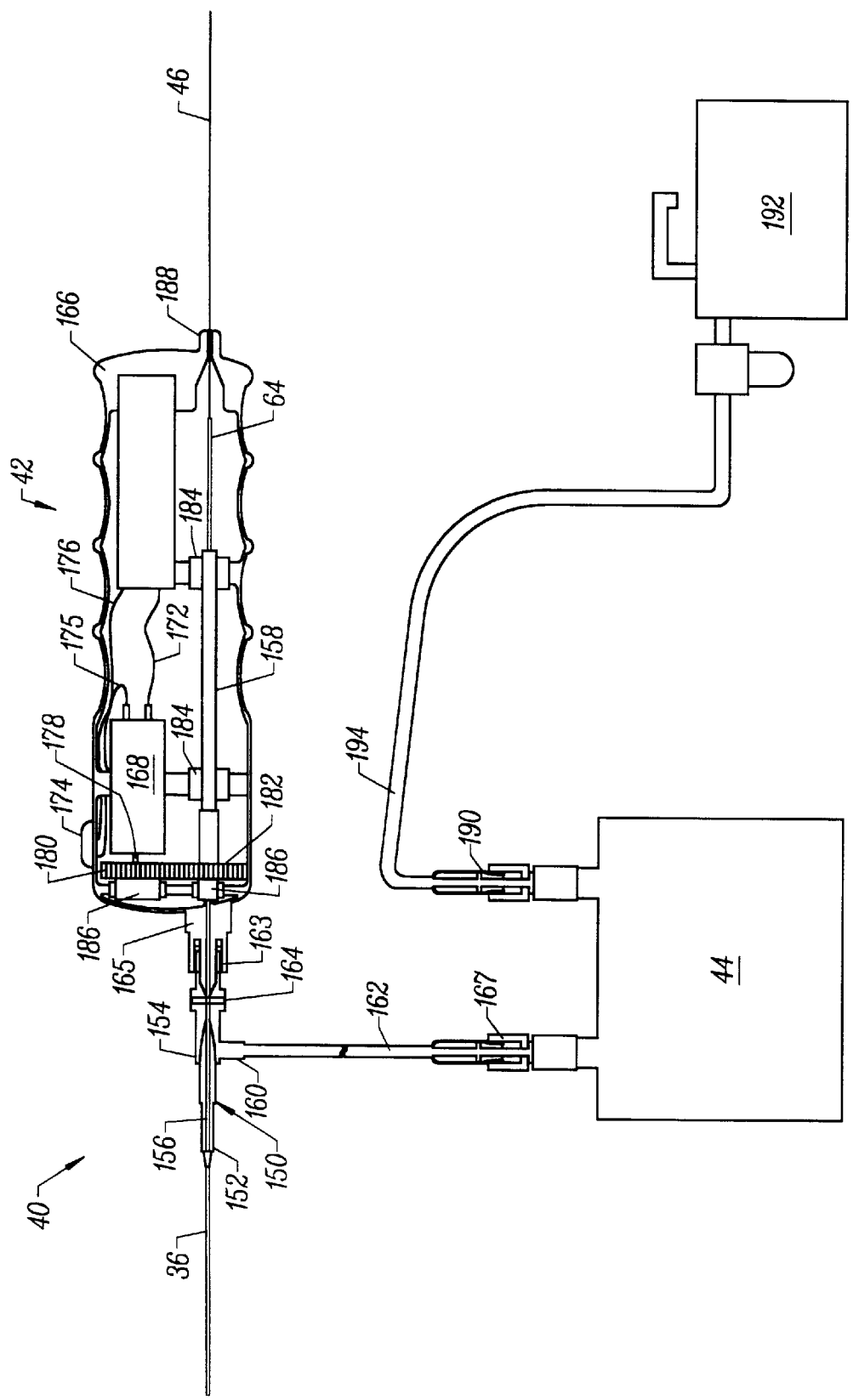
FIG. 7 is an enlarged sectional view of a proximal connector assembly, a hand-held unit, and a collection reservoir that can be used with the system of FIG. 1.

The torque member 52 is illustrated in greater detail in FIG. 4. The torque member 52 includes three layers of counterwound wires that form concentric coils. These three coiled layers include an inner coil 56, a middle coil 58 and an outer coil 60, all of which are secured together. In the embodiment illustrated in FIG. 4, the inner coil 56 is wound counterclockwise in a helical direction that is opposite to the clockwise helical winding direction of the middle coil 58. The inner coil 56 defines a hollow guidewire lumen 62. The inner coil 56 and the middle coil 58 operate together to transmit torque. The proximal end 64 of the middle coil 58 is rotatably connected to the hand-held device 42, as shown in FIG. 7 and described in greater detail hereinbelow. When the middle coil 58 is rotated in a clockwise direction, it attempts to become diametrically smaller due to its clockwise winding direction. At the same time, the counterwound inner coil 56 attempts to become diametrically larger, again due to its counterclockwise winding direction. This creates a rotational engagement between the inner and middle coils 56, 58 that causes the coils 56 and 58 to lock together to create a reliable torque transmission member. This engagement between the inner and middle coils 56, 58 provides a torque transmission member which exhibits excellent torsional rigidity while allowing the torque member 52 to remain sufficiently flexible to navigate the tortuous paths of a patient's vasculature.

The inner and middle coils 56 and 58 are provided in filar groupings. FIG. 4 illustrates a quadrafilar coil construction (i.e., four wires wound together) for the inner and middle coils 56 and 58, but filar groupings having any number of wires wound together can also be chosen, depending on the requirements of the application. In this regard, the determination of the number of wires in a filar grouping is based on balancing three basic considerations. The first consideration relates to the inherent flexibility associated with a given number of wires in a group. In general, a more flexible torque member 52 is achieved if fewer wires are provided in each filar grouping. The second consideration relates to the total number of desired winds along the length of the torque member 52. For example, it would take fewer total winds (which translates to less manufacturing time) to manufacture a quadrafilar as opposed to a unifilar torque member 52 of the same length. The third consideration relates to energy storage when in torsion. With fewer wires in a grouping, greater rotational energy is stored along the length of the torque member. In other words, there is a phenomenon called "wind-up" (an input perspective) or "whip" (an output perspective) which requires more rotations at the proximal end before the distal end begins to follow. In general, when designing a torque member, it is desirable for the output (i.e., distal rotational performance) to closely follow the input (i.e., proximal rotational extent). The more wires in a grouping, the less torsional preload is required before the distal end follows the proximal end.

The inner and middle coils 56 and 58 can have the same or different helical angles and spacings. The helical angle used for the inner and middle coils 56 and 58 can range from approximately 5 to 85 degrees with respect to the longitudinal axis, and can be chosen based on the torque requirements of the application and the tortuosity of the patient's vasculature. The spacing between coils 56 and 58 can range from zero to the width of a filar grouping, and are also chosen based on the requirements of the application. The helical angles and spacings for the inner and middle coils 56 and 58 are also related to and contribute to the "wind-up" phenomenon. For example, it is easier to achieve a tighter filar group spacing if the helical angle is steeper. There are also additional considerations. For example, steeper helical angles require the use of more wire, require greater wind-up, and achieve a more flexible torque member 52. Conversely, shallower helical angles require the use of less wire and require less wind-up. Shallower helical angles also occupy more radial space in a given torque member 52 because the "filar group ribbon" has to "twist", rather than lay flat, to achieve the shallower angle.

The outer coil 60 is not relied on to contribute to the torque transmission, but is used as part of a conveyor mechanism to transport separated and removed occluding material from the removal mechanism 54 along the lumen 50 of the catheter 32, and ultimately outside the patient's body to the collection reservoir 44. The transportation of separated and removed occluding material outside the patient's body is referred to hereinafter as "extraction". The outer coil 60 and the inner surface 66 of the lumen 50 together form a conveyor. To function as an effective conveyor, the diameter of the lumen 50 is selected to bring the inner surface 66 in close proximity to the outermost surface of the outer coil 60. The outer coil 60 is wound over the middle coil 58 in a winding direction that is opposite from the winding direction of the middle coil 58. The outer coil 60 is wound at about the same direction, and can even be wound at the same range of angles, as the inner coil 56. The outer coil 60 is spaced to form helical flutes 68 having a spacing 69 between adjacent windings in the outer coil 60. The spacing 69 is uniform throughout its length, and is chosen so that it forms a helical annulus through which fluid (e.g., saline, blood, Ringer's Solution, etc.) and excised occluding material can pass in an unrestricted manner. In particular, the spacing 69 is chosen so that the size of the largest tissue fragments that are separated and removed can travel unimpeded through the helical flutes 68. The arrangement and positioning of the outer coil 60 and the inner surface 66 of the catheter lumen 50 create an Archimedes-type of "screw pump". The utilization of this "screw-pump" arrangement can obviate the need for external aspiration, although an externally connected aspiration device (as described below) can be used to supplement and enhance the tissue extraction function of the "screw pump".

The winding directions of the inner, middle and outer coils 56, 58, 60 have been illustrated as being intended for clockwise rotation. If counter-clockwise rotation of the torque member 52 is desired, the winding directions for the inner, middle and outer coils 56, 58, 60 should be reversed.

Figure 4A:
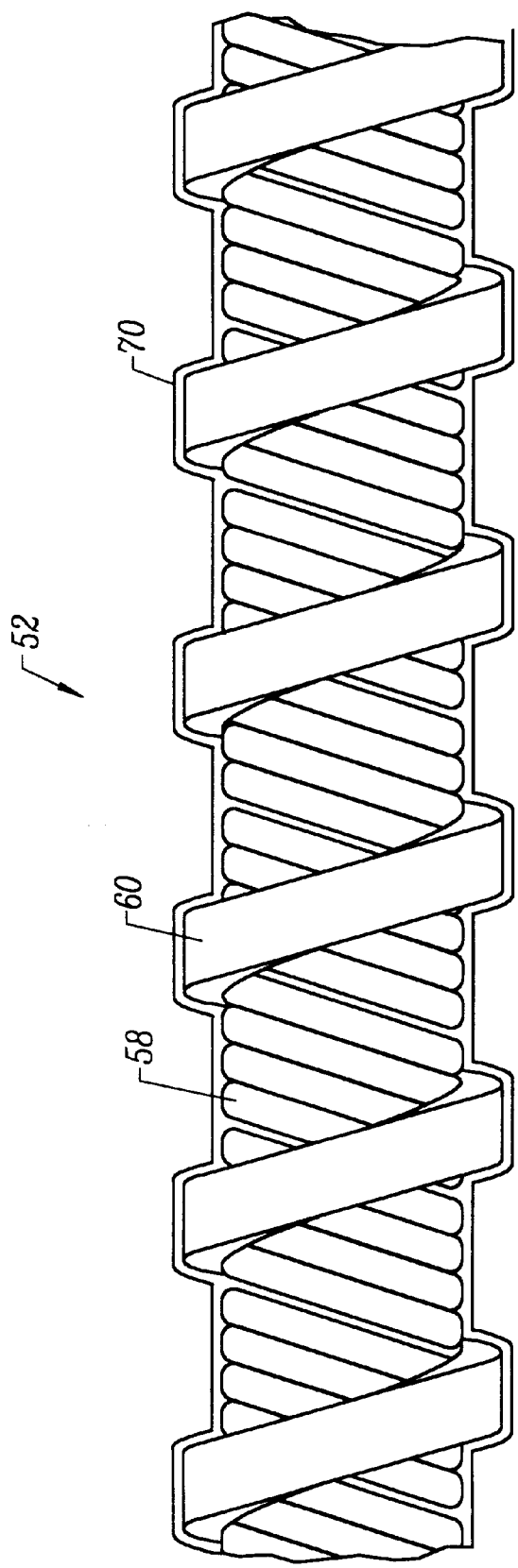
FIG. 4A is a partial side view of the torque member of FIG. 4 illustrating the torque member encased in a polymer jacket.
Figure 4B:
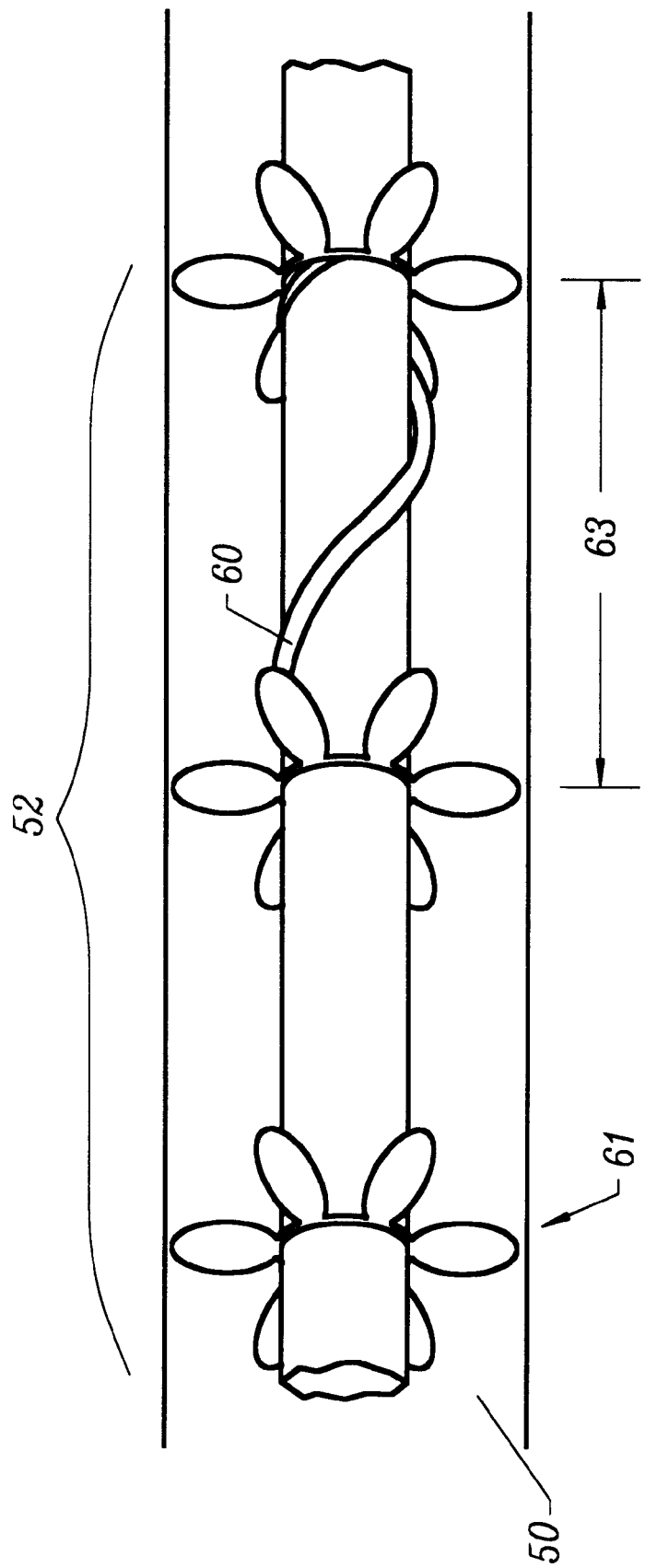
FIG. 4B is a partial side view of a alternative torque member configuration that can be used with the system of FIG. 1.

The inner, middle and outer coils 56, 58, 60 can be formed from suitable wire materials such as stainless steel and other metals that are biocompatible and that are resistant to kinking. In addition, these coils 56, 58 and 60 can have a circular or ribbon-like cross-section. FIG. 4B shows a modified configuration where wire 60 is replaced with a series of spaced impellers 61 to provide liquid pumping inside the lumen 50. The impellers 61 are fixedly attached to the torque member 52 and are pitched so fluid is pumped out of the body when the torque member 52 is rotationally engaged. Note it is possible to use wire 60 and impellers 61 in conjunction by creating cells where wire 60 runs for a predetermined length and are separated by impellers 61 as cell separators. Said cells being defined by a distance 63 between impellers 61.

It can be beneficial to encase the three layers of coils 56, 58, 60 in a polymer jacket 70 (see FIG. 4A), which serves to secure the coils 56, 58, 60 together. The polymer jacket 70 can be applied through one of a number of approaches. For example, the polymer jacket 70 can take the form of a thermoplastic sleeve which is melted around the coils 56, 58, 60 to fill their interstices and to create a barrier between the guidewire lumen 62 and conveyor defined by the outer coil 60 and the inner surface 66. Alternatively, the polymer jacket 70 can be a thermoplastic or thermosetting sleeve with shape-memory characteristics (e,g., cross-linked polyolefins, polyesters, fluoropolymers, etc.) that are shrunk onto the triple coil 56, 58, 60 assembly. As yet another alternative, the polymer jacket 70 can be a thermoset, such as polyimide, which is applied through dipping, casting, spraying, brushing or other similar techniques. In applications where the torque member 52 must be provided with a small size and profile, other thin thermoplastic jackets, such as parylene, can be vacuum deposited onto the torque member 52 and used as the polymer jacket 70.

The outer coil 60 does not need to be provided as a separate wire. For example, it is also possible to encase the inner and middle coils 56, 58 using any of the methods and polymeric materials described above, and then the outer coil 60 can be formed by selectively removing polymeric material to form the helical configuration of the outer coil 60. This selective removal of polymeric material can be accomplished by using any known method, such as by cutting external threads on a lathe.

2. The Removal Mechanism 54 and The Bearing Assembly 100

A removal mechanism 54 is secured to the distal end 72 of the torque member 52. The removal mechanism 54 is used to excise occluding material from the luminal wall of a blood vessel or other body lumen. Excision can be accomplished by cutting, shearing, coring, scraping, or other known methods. The function of the removal mechanism 54 is to separate the occluding material from the luminal wall of a blood vessel, so that the occluding material can then be removed and extracted from the patient's vasculature.

One embodiment of a removal mechanism 54 is illustrated in FIGS. 2 and 3. The removal mechanism 54 in FIGS. 2 and 3 is a rotatable helical cutter. The helical cutter 54 has a plurality of counterclockwise helical turns 74 defining a lumen extending longitudinally therethrough, and shearing aspects extending longitudinally therealong. The helical turns 74 have a proximal cutting edge 76 that is adapted to cut occluding material during clockwise rotation of the helical cutter 54. In other words, the proximal edge 76 is in effect the leading edge when the cutter 54 is rotated in the clockwise direction. The number of helical turns 74 depends on the smoothness of the desired cut and the "aggressiveness" with which tissue is to be removed. In this regard, "aggressiveness" is defined as the degree of engagement of the removal mechanism 54 with the occluding material. For example, increasing the number of helical turns 74 over the same axial length provides a smoother cut, while decreasing the number of helical turns 74 provides a more aggressive cut. If the helical cutter 54 is to be rotated counter-clockwise, then the helical turns 74 should be spiraled in an opposite direction (i.e., in this case, clockwise).

The helical cutter 54 is secured to the distal end 72 of the torque member 52 in the following manner. Referring to FIGS. 3–4, a length of the distal portions of the middle and outer coils 58 and 60 are peeled or cut back to a circumferential point 82 to expose a distal length 84 of the inner coil 56. This is illustrated in FIGS. 3 and 4, where the middle and outer coils 58 and 60 are shown as extending from their proximal ends to a distal-most extent defined by the circumference 82. The distal-most ends 86 and 88 of the middle and outer coils 58 and 60, respectively, are then dressed and subsequently secured (e.g., by welding, soldering, brazing or gluing) to prevent the middle and outer coils 58 and 60 from unravelling. The helical cutter 54 is then slid over the exposed distal length 84 of the inner coil 56 so that the inner coil 56 is received inside the lumen of the helical cutter 54, and the proximal end 90 of the helical cutter 54 is secured to the distal ends 86 and 88 of the middle and outer coils 58 and 60, respectively, by brazing, soldering, welding, adhesive bonding, or any other conventional methods. The distal end 92 of the helical cutter 54 is also secured, using one of the methods described above, to the outer surface of the inner coil 56 at a location slightly proximal from the distal tip 94 of the inner coil 56. It is also possible to secure the inner surfaces of the helical turns 74 along the outer surface of the inner coil 56. The flutes 96 defined between the helical turns 74 communicate with the flutes 68 of the outer coil 60 to deliver dislodged or cut occluding material to the conveyor defined by the outer coil 60 and the inner surface 66.

The torque member 52 is positioned inside the lumen 50 of the catheter 32 such that it extends longitudinally therethrough with most of the exposed distal length 84 of the inner coil 56 extending distal from and outside of the distal end 38 of the catheter 32. Therefore, the helical cutter 54 also extends partially outside of the catheter body 34. A bearing assembly 100 is provided to secure the distal end 72 of the torque member 52, and the removal mechanism 54 secured thereat, at a fixed axial position at the distal end 38 of the catheter body 34 while simultaneously allowing rotation of the torque member 52 and the removal mechanism 54.

Referring now to FIGS. 2 and 5–6, the bearing assembly 100 includes a resilient snap ring 102 and an overlying shell 104. The snap ring 102 is best illustrated in FIGS. 3 and 5, and has a cylindrical body 106 with an inner rib 108 extending circumferentially about an inner surface 110 of the cylindrical body 106. One longitudinal slit 112 can be provided along the cylindrical body 106 to allow the ring 102 to be compressed or radially expanded. The rib 108 is adapted to be fitted inside a circumferential groove 114 provided near the proximal end 90 of the helical cutter 54. The snap ring 102 is preferably made of stainless steel or other resilient alloys, and is preferably biocompatible and offers good resistance to fatigue resulting from elastic or plastic deformation.

The shell 104 is best illustrated in FIGS. 3 and 6, and has a generally cylindrical body 120 having an annular distal lip 122 that extends radially inwardly to narrow the distal opening 124 of the cylindrical body 120. A ramp 126 extends from the proximal end of the cylindrical body 120 and ramps radially inwardly to form a cylindrical barbed section 128 which has a diameter that is smaller than the diameter of the cylindrical body 120. A plurality of barbs 130 are provided on the outer surface 132 of the cylindrical barbed section 128. The shell 104 is preferably made of stainless steel or other resilient alloys, and is preferably biocompatible.

To assemble the bearing assembly 100, the snap ring 102 is first secured to the proximal end 90 of the helical cutter 54, and the shell 104 secured to distal end 38 of the catheter 32, before the snap ring 102 is fitted inside the shell 104.

Specifically, the torque member 52 and the proximal end 90 of the helical cutter 54 are first slid into the lumen of the cylindrical body 106 of the snap ring 102 until the circumferential rib 108 is fitted or seated inside the circumferential groove 114. The resiliency of the cylindrical body 106 provided by the slit 112 allows the body 106 to be stretched to permit the proximal end 90 of the helical cutter 54 to pass therethrough and over its rib 108 until the groove 114 receives the rib 108.

At the same time, the barbed section 128 of the shell 104 is slid inside the lumen 50 at the distal end 38 of the catheter body 34. The barbs 130 engage the inner surface 66 of the catheter body 34 to form a secure barb-hose type connection. The distal extremity of the catheter body 34 can be slid over the outer surface 132 of the barbed section 128 until it reaches the ramp 126, which acts as a stop that defines the limit of distal advancement of the catheter body 34 along barbed section 128. In addition, the outer surface 134 of the cylindrical body 120 of the shell 104 is preferably aligned with the outer surface 136 of the catheter body 34 to provide a smooth transition between the shell 104 and the catheter 32.

At this time, the distal lip 122 of the shell 104 is slid over the snap ring 102. Since the distal opening 124 of the cylindrical body 120 has a diameter which is smaller than the diameter of the cylindrical body 106 of the snap ring 102 in its normal relaxed state, the cylindrical body 106 will need to be radially compressed to allow the distal lip 122 to pass over it. The longitudinal slit 112 provides the resiliency to allow the cylindrical body 106 to be radially compressed without buckling its structure. Once the distal lip 122 has passed over the entire cylindrical body 106 of the snap ring 102, the resilient nature of the snap ring 102 will cause the cylindrical body 106 to spring back to its normal relaxed state, in which it will be seated inside the shell 104 between the distal lip 122 and the ramp 126, creating a secure interference fit.

Alternatively, the bearing assembly 100 can be assembled by first sliding the snap ring 102 inside the shell 104 in the manner described above. The shell 104 can then be secured to distal end 38 of the catheter 32, and the helical cutter 54 secured to the snap ring 102 using the methods described above.

The bearing assembly 100 performs two functions. First, the distal lip 122 and the ramp 126 together provide thrust confinement for a thrust bearing that consists of the snap ring 102 inside the shell 104. Second, the interaction between the snap ring 102 (which is securely coupled to the helical cutter 54 and the inner coil 56) and the shell 104 (which is securely coupled to the catheter body 34) provides smooth rotational bearing surfaces. In this manner, the rotational engagement between the rib 108 and the groove 114 allows the helical cutter 54 to rotate together with the inner coil 56, while the interference fit of the snap ring 102 inside the shell 104 between the distal lip 122 and the ramp 126 prevents axial displacement of the helical cutter 54 and the inner coil 56 with respect to the catheter body 34. The interface and interaction between the shell 104 and the snap ring 102 further enable the catheter body 34 to not be rotated when the torque member 52 and the helical cutter 54 are rotated.

3. Proximal Connector Assembly 40, Hand-Held Device 42 and Collection Reservoir 44

Referring now to FIGS. 1 and 7, the proximal connector assembly 40 of the system 30 has an elongate, rigid body 150 defining frontal and rear portions. The frontal portion 152 of the body is firmly connected to the proximal end 36 of the catheter body 34. The proximal end of the frontal portion 152 is connected to the distal end of the rear portion 154 of the body 150. A lumen or passageway 156 extends longitudinally through the frontal portion 152 and the rear portion 154, and communicates with a hollow lumen inside a rotator shaft 158 provided inside the hand-held device 42. The torque member 52 extends through the passageway 156 and is secured inside the lumen of the rotator shaft 158. The rigid body of the proximal connector assembly 40 has a side arm 160 which is connected, by way of a tube 162, to a collection reservoir 44. A dynamic seal 164 is provided in the rear portion 154 to act as a seal around the torque member 52 to prevent fluid flow through the passageway 156 into the hand-held device 42, and to ensure that all occluding material and fluids (such as blood) are diverted to the side arm 160 and the collection reservoir 44. The dynamic seal 164 can be implemented in the form of an O-ring, or a perforated gasket of an elastomeric material, either synthetic (e.g., silicone) or naturally occurring (e.g., natural rubber). A conventional male-female luer fitting 163 is also provided in the rear portion 154 to connect the proximal connector assembly 40 to a front portion 165 of the hand-held device 42.

The hand-held device 42 has a housing 166 that houses a motor 168 and a battery 170. The battery 170 provides electrical energy to the motor 168 via wire leads 172. A control switch 174 is coupled to the motor 168 and the battery 170 by similar wire leads 175 and 176, respectively, to control the operation of the motor 168. The motor 168 has a shaft 178 which carries a first driving gear 180 that rotatably engages a second gear 182 to rotatably drive the second gear 182. The second gear 182 is carried on the rotator shaft 158 so that rotation of the first driving gear 180 will cause the second gear 182 to rotate the rotator shaft 158, thereby rotating the torque member 52 retained therein. A first plurality of rotator shaft bearings 184 are provided to facilitate rotation of the rotator shaft 158, and a second plurality of gear bearings 186 are provided to facilitate rotation of the gears 180 and 182. The proximal end of the guidewire 46 extends from the proximal end 64 of the torque member 52 inside the hand-held device 42 and through an opening 188 provided at the proximal end of the housing 166 out of the hand-held device 42 to allow the physician to perform guidewire exchange and to manipulate the guidewire 46, as described in greater detail hereinbelow.

The collection reservoir 44 may be a ceramic or polymeric container that is transparent so that the physician can visually determine the fill volume of the reservoir 44. A first conventional male-female luer fitting 167 connects the tube 162 to the collection reservoir 44. The conveyor mechanism defined by the outer coil 60 and the inner surface 66 of the lumen 50 will cause occluding material to be conveyed from the distal end 38 of the catheter 34 to the rear portion 154 of the proximal connector assembly 40, where the occluding material will be diverted by the dynamic seal 164 into the collection reservoir 44 by the action of the "screw pump".

It is also possible to provide aspiration to the region of the blood vessel where the occluding material is being treated, even though the "screw pump" defined by the outer coil 60 and the inner surface 66 of the catheter lumen 50 may be sufficient to completely remove all separated occluding material from the blood vessel. This can be accomplished by providing the collection reservoir 44 with a second conventional male-female luer fitting 190 that is connected to a vacuum pump 192 via a pump tube 194. Such aspiration will enhance the extraction of the excised occluding material.

4. Guidewire 46

The catheter 32 is preferably configured to operate in an over-the-wire mode. The catheter 32 can be used with conventional guidewires to form an initial pilot lumen equivalent in size to the outer diameter of the catheter 32 and the removal mechanism 54. The conventional guidewire can then be exchanged for the guidewire 46 of the present invention.

Figure 8:
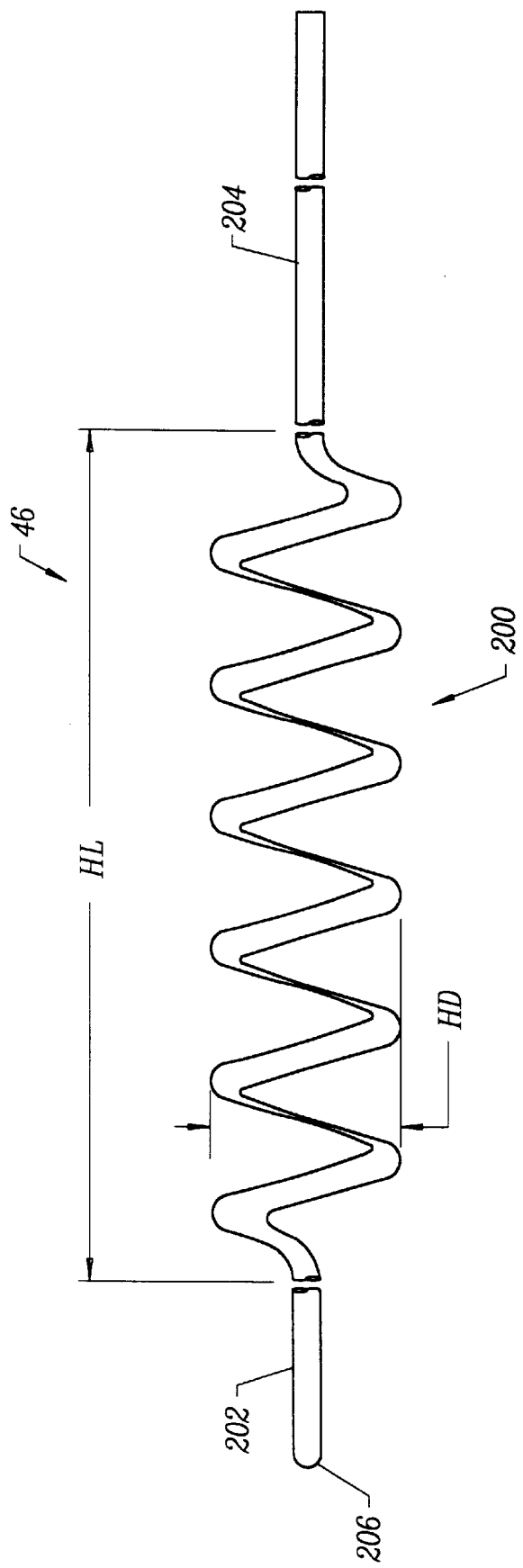
FIG. 8 is a side view of the distal end of a guidewire that can be used with the system of FIG. 1.

FIG. 8 illustrates an embodiment of a guidewire 46 that can be used with the system 30 of the present invention. The guidewire 46 is preferably provided with a configuration to enable it to guide, in a controlled manner, a removal mechanism 54 at and along the location of the occluding material for separating and removing portions of the occluding material, so as to create a series of sculpted conduits through an obstructed vessel lumen. The resulting passageway created through the obstruction would be diametrically larger than the outer diameter of the removal mechanism 54 and the catheter 32.

Figure 8B:
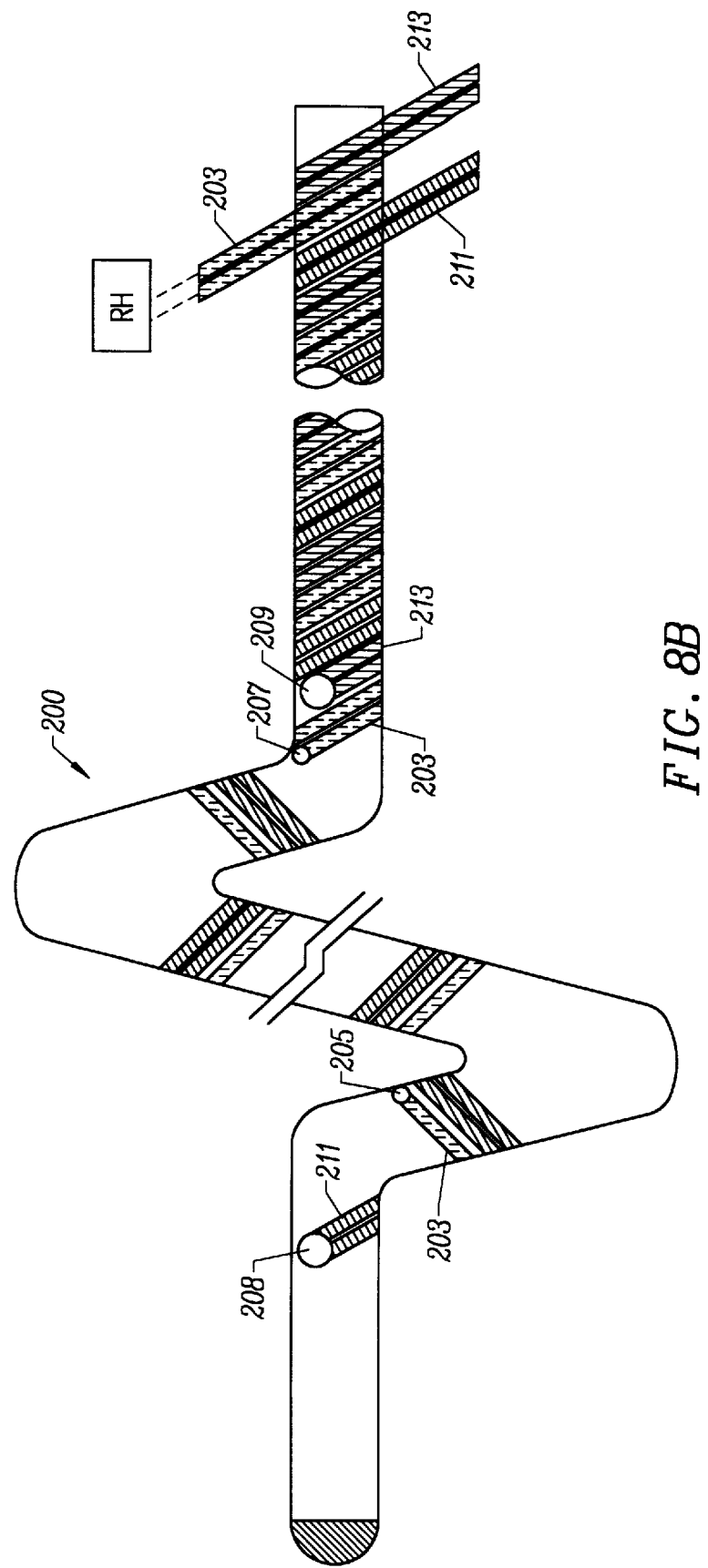
FIG. 8B is a side view of portions of the helical section of the guidewire of FIG. 8 when the guide section of the guidewire is expanded by proportional control.
Figure 8C:
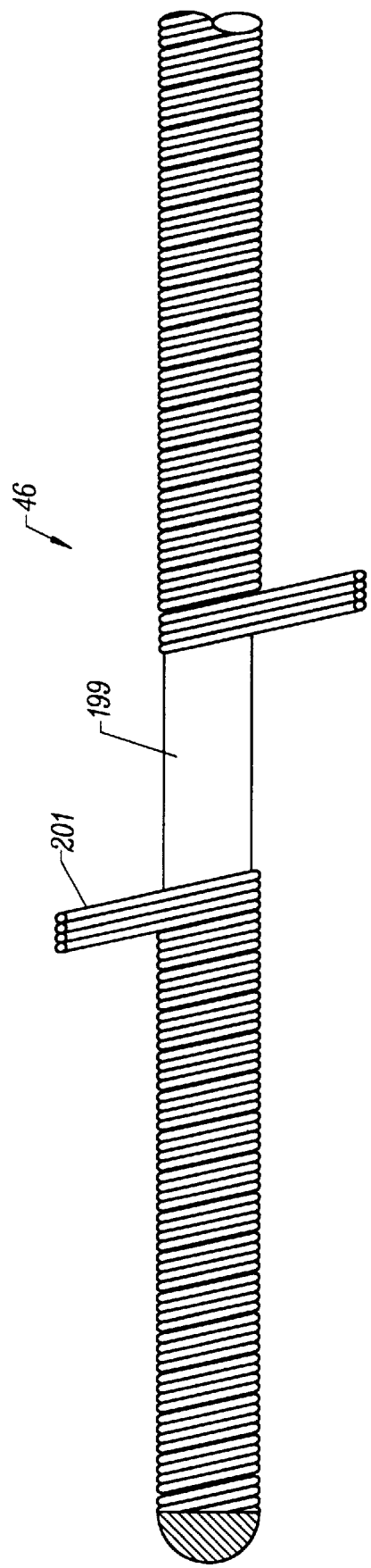
FIG. 8C is an exploded side view of a portion of the guidewire of FIG. 8.

Referring to FIGS. 8, 8A, and 8C, the guidewire 46 is provided with a generally helical distal guide section 200 adjacent its distal end 202. As shown in FIG. 8A, the helical distal guide section 200 has a three-dimensional configuration that approximates the configuration of a luminal wall. The distal end 202 of the guidewire 46 is generally straight and preferably has an atraumatic distal tip 206. The remainder of the guidewire 46, and in particular, the proximal section 204, is generally straight, as with conventional guidewires. The distal section 202 and the proximal section 204 are axially coplanar with each other, and are preferably coaxial with respect to each other. In other words, the distal section 202 and the proximal section 204 are oriented along the same longitudinal axis. In addition, the distal section 202 and the proximal section 204 are concentric, and can also be eccentric, with respect to the guide section 200. The proximal and distal extremities of the guide section 200, or the entire helical section, are preferably provided with sufficient radiopacity so that the guide section 200 can be clearly viewed during fluoroscopic visualization. The radiopacity can be provided by the use of a radiopaque wire 201, as shown in FIG. 8C, which can be made of platinum or gold alloys or other radiopaque wires, and which is wound around the core 199 forming the helical turns of the guide section 200.

The guidewire 46 is intended to allow the catheter 32 and the removal mechanism 54 carried thereon to follow the helical configuration of the helical guide section 200 so as to bring the removal mechanism 54 in contact with the inner luminal wall of the blood vessel to be treated. After sequential passes with the catheter 32 and removal mechanism 54 along the helical guide section 200, and sequential axial translations of the guidewire 46, a passageway in the lumen of the blood vessel is formed whose diameter is generally equal to the sum of the diameter of the helical guide section 200 and twice the depth of the cuts, shears or slices of the occluding material taken by the removal mechanism 54.

The core 199 of the guidewire 46, and in particular, its guide section 200, are preferably formed using materials of a composition, processing regimen, shape and dimension that operate over a range within the material's elastic limit. Specifically, the materials used for the guide section 200 preferably operate within a range defined by a lower boundary of yield stress and an upper boundary of the elastic limit of the material, and in particular, a material having a sufficiently wide range of deformation (e.g., approximately up to 8%) upon which full recovery can still be achieved. "Yield stress" as used herein means the stress level at which a finite strain is first observable. "Stress" can be defined as an applied force or system of forces that tends to strain or deform a body. "Strain" can be defined as a deformation produced by stress. "Elastic limit" as used herein means the stress level at which permanent or plastic deformation takes place.

Thus, a guide section 200 that is provided with a material operating within the material's yield stress and elastic limit will have a preformed shape that is adaptable to essentially any inner open space of a generally tubular or duct-like passageway, and in particular, to lumen shapes varying from true cylindrical to substantially non-cylindrical. Such a guide section 200 is capable of being elastically (but not plastically) deformed in order to pass it through the guidewire lumen 62 of the torque member 52, and is capable of recovering its full configuration inside the passageway of the stenosis or lumen.

As a result, the pitch (i.e., wavelength) and the helical diameter HD (i.e., amplitude) of the helical guide section 200 are preferably dynamically adaptable to the changing geometries of a passageway within a stenosis or body lumen. For example, the pitch to diameter ratio preferably in the range from 0.1:1 to 5:1, and in one embodiment is 1:1. The pitch and the helical diameter HD of the helical section are preferably changed as the volume of the occluding material is reduced. Specifically, the pitch is looser, and helical diameter HD is smaller, when the volume of the occluding material is greatest (i.e., the passageway through the occluding material is smallest). As the volume of the occluding material is reduced, the pitch preferably becomes tighter and the helical diameter HD greater.

In addition, the maximum diameter HD of the helix in the helical guide section 200 is preferably chosen to be equal to or slightly larger than the body lumen in which it is to be deployed for treatment although, as explained below, varying diameters can be provided depending on the mode of operation utilized. The helical angles for the helical guide section 200 are also chosen such that the rigid length of the removal mechanism 54 has minimal impact on elastically deforming the helical turns of the helical guide section 200 as the removal mechanism 54 traverses the helical guide section 200. The overall length HL of the helical guide section 200 is preferably chosen to be slightly longer than the length of the occluding material to be traversed.

One example of a material that can be used for the guide section 200 is a shape memory alloy such as nickel-titanium (NiTi). NiTi exhibits superelastic properties and increased flexibility over conventional stainless steel which will ease the insertion of the helical guide section 200 through the guidewire lumen 62. NiTi allows for more precise axial positioning adjacent to an already removed helical conduit or track by conforming more readily to the body lumen being treated.

Examples of superelastic metal alloys, including NiTi, which are usable to form the core 199 of the guidewire 46 of the present invention are described in detail in U.S. Pat. No. 4,665,906. The disclosure of U.S. Pat. No. 4,665,906 is expressly incorporated herein by reference insofar as it describes the compositions, properties, chemistries, and behavior of specific metal alloys which are superelastic within the temperature range at which the guide section 200 of the guidewire 46 of the present invention operates, any and all of which superelastic metal alloys may be usable to form the core 199 of the guide section 200 of the guidewire 46.

When NiTi is used to form the core 199 of the helical guide section 200 of the guidewire 46, the helical guide section 200 of the guidewire 46 is provided in its original helical configuration having its maximum helical diameter. The guidewire 46 is then mechanically deformed to a generally straight configuration so that it can be easily inserted through the guidewire lumen 62. After the guidewire 46 has been introduced into a blood vessel for use according to the methods described hereinbelow, the helical guide section 200 is caused to return to its original helical configuration, at either its maximum helical diameter or at varying helical diameters. Depending on the operation mode employed, as described below, this can be accomplished by thermally inducing the helical guide section 200 to cause it to return to its helical configuration (either its maximum diameter or at varying helical diameters), or by releasing the forces that hold the helical guide section 200 in the generally straight configuration.

A helical guide section 200 having at least a core made from NiTi can be employed in one of the following modes: superelastic, constrained recovery without proportional control, and constrained recovery with proportional control. These terms are now defined.

The term "superelasticity" means the property of certain alloys to return to their original shape upon unloading after a substantial deformation. Superelastic alloys such as NiTi can be strained ten times more than ordinary spring materials without being plastically deformed. With respect to the guidewire 46, the "superelastic" mode means a NiTi core helical guide section 200 that has an original helical configuration, is deformed when it is held in a generally straight configuration, and which returns to its original helical configuration when it is released from the forces that have held it in the generally straight configuration.

"Constrained recovery" means a NiTi core helical guide section 200 having a maximum diameter that is greater than or equal to the diameter of the luminal passageway in which it is deployed when it is returned to its original helical configuration at its maximum helical diameter. Again, this luminal passageway can be the passageway created through the occluding material. In other words, the helical guide section 200 is "constrained" in that it contacts the luminal passageway when it "recovers" its original helical configuration.

"Proportional control" means that the recovery of the helical guide section's 200 original helical configuration is proportionally controlled so that the helical guide section 200 is induced to proportionally progress from the straight configuration to its maximum and full helical diameter over a continuum.

Proportional control can be accomplished by titrating the amount of thermal energy applied to the helical guide section 200. For example, heat can be applied to the helical guide section 200 by bathing the helical guide section 200 in a physiologically inert fluid (e.g., saline, Ringer's Solution, etc.) that is introduced via the lumen of a guide catheter (not shown) through which the catheter 32 is introduced. Alternatively, heat can be applied to the helical guide section 200 by passing current through the guidewire 46 from its proximal end 204. This can be accomplished by attaching one or two leads to the helical guide section 200. For example, referring to FIG. 8B, a lead pair 203 is connected to a source of heat, such as a resistance heater RH. The lead pair 203 has a distal lead attachment 205 and a proximal lead attachment 207 provided on the distal and proximal extremities, respectively, of the helical guide section 200.

In addition, temperature sensors (e.g., thermocouples or thermistors) can be provided integrally with or in the vicinity of the helical guide section 200 for closed loop feedback to an appropriate electrical circuit during energy titration. One possible arrangement would be to place a distal temperature sensor 208 and a proximal temperature sensor 209 on the distal and proximal extremities, respectively, of the helical guide section 200 (see FIG. 8B). Each temperature sensor can be either a thermocouple or a thermistor. Distal temperature sensor 208 is coupled to a first thermocouple or thermistor thermometry circuit via a first lead pair 211, and proximal temperature sensor 209 is coupled to a second thermocouple or thermistor thermometry circuit via a second lead pair 213. The temperature sensing elements 208, 209 measure the temperature gradient across the helix of the helical guide section 200. This temperature sensing placement approach takes advantage of the available space within a 0.014 inch or other conventional size guidewire diameter and the temperatures measured would accurately represent the phase transformation correlation with the helical diameter of the helical guide section 200. Proportional control would reduce the number of guidewires 46 required for the procedure, as will become more evident in the description of the methods of the present invention hereinbelow.

Any of the NiTi wires used as the guidewire core 199 described above (i.e., superelastic, constrained recovery without proportional control, and constrained recovery with proportional control) are available in the market and can be obtained, for example, from Raychem Corp. of Menlo Park, Calif.

The helical guide section 200 of the guidewire 46 can be modified so that it has a generally tapered or stepped, or both tapered and stepped, configuration. For example, the helix of the guide section 200 can be tapered from the proximal extremity to the distal extremity thereof so that the helical diameter decreases from the proximal extremity to the distal extremity. The helix can also be stepped at certain discrete locations of the guide section 200. In addition, although the helical guide section 200 of the guidewire 46 is illustrated as having uniformly configured helixes, it is also possible to provide the helixes in a manner that they are non-uniform to each other across the helical length HL.

As a further alternative, the guide section 200 need not be provided in a helical configuration. Referring to FIG. 8C, the guide section 200a has a polygonal configuration in three-dimensional space.

As yet another alternative, a plurality of guide sections 200 can be provided in spaced-apart manner at the distal end of the guidewire 46. For example, two spaced-apart guide sections 200 would be helpful in treating body lumens where restenosis has occurred at the locations of two spaced-apart implanted stents.

5. Alternative Removal Mechanisms

Figure 9D:
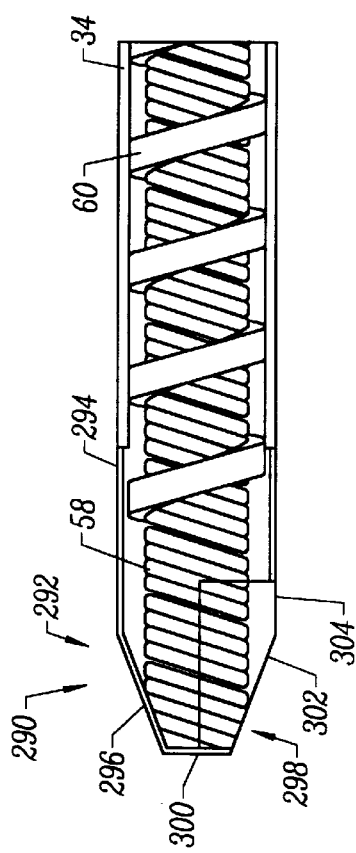
FIGS. 9A–9D illustrate different embodiments of removal mechanisms that can be used with the system of FIG. 1.
Figure 9C:
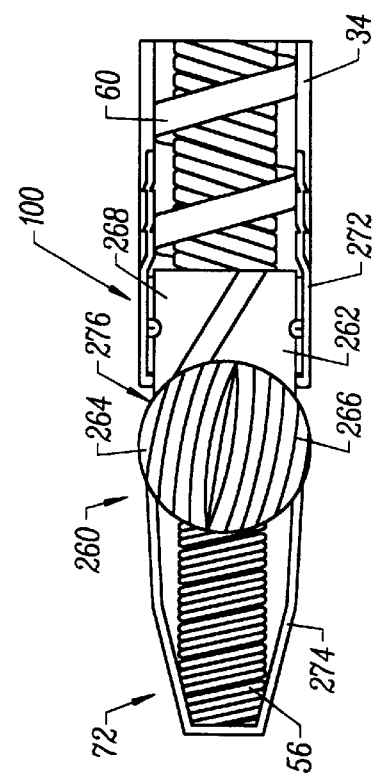
Figure 9B:
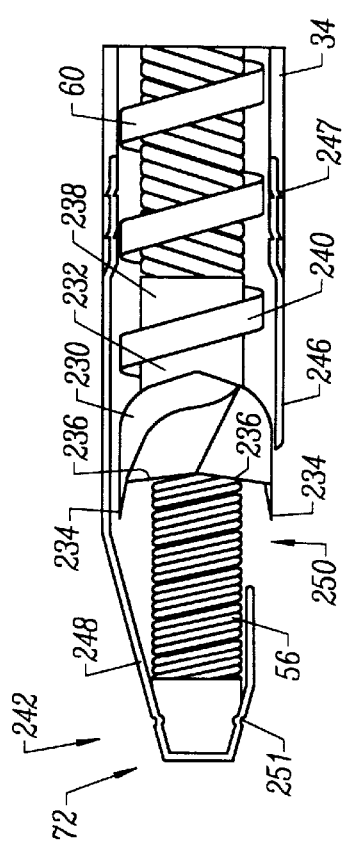
Figure 9A:
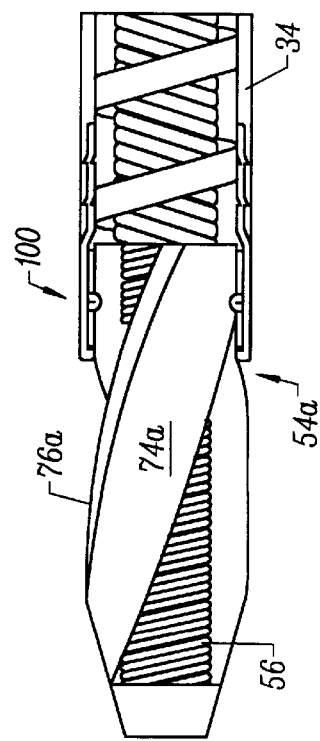

A number of alternative removal mechanisms 54 are illustrated in FIGS. 9A–9D. FIG. 9A illustrates another helical cutter 54a which is similar to the helical cutter 54 illustrated in FIGS. 2 and 3, except that helical cutter 54a has a shallower helix angle while the helical cutter 54 has a steeper helix angle. As a result, helical cutter 54a has fewer helical turns 74a. The helical turns 74a likewise have a proximal cutting edge 76a that is adapted to cut occluding material during clockwise rotation of the helical cutter 54a. If the helical cutter 54a is to be rotated counter-clockwise, then the helical turns 74a will need to be wound in the opposite direction. The helical cutter 54a is secured to the exposed distal length 84 of the inner coil 56 according to the same method described above. A bearing assembly, such as bearing assembly 100, described above, is also preferably provided at the connection between the catheter body 34 and the helical cutter 54a.

FIG. 9B illustrates a Forstner cutter 230 that can be used to core a passageway through the occluding material. The Forstner cutter 230 is defined by a cylindrical shaft 232 having a widened annular coring blade or cutting edge 234 provided at the distal end. A plurality of scraping surfaces 236 are positioned about 180 degrees apart to break apart the occluding material that has been cored by the coring blade 234. The cutter 230 is connected to the inner coil 56 of the torque member 52 by sliding the distal end 72 of the inner coil 56 through the hollow lumen of the cylindrical shaft 232, and securing the proximal end 238 of the cylindrical shaft 232 to the distal ends 86 and 88 of the middle and outer coils 58 and 60, respectively. A helical turn 240 is provided at the proximal end 238 of the cylindrical shaft 232 to facilitate the transportion of occluding material from the cutter 230 to the conveyor defined by the outer coil 60 and the inner surface 66 of the catheter body 34. The cutter 230 is housed inside a cutter housing 242, which is provided in the form of a tapered cylindrical body having a proximal cylindrical section 246 inside which the cutter 230 is housed, and a tapered distal section 248. The proximal end of the proximal cylindrical section 246 is affixed to the distal end 38 of the catheter body 34 by adhesive bonding, a barbed-hose connection 247 (see FIG. 9B), or other similar affixation means, or the proximal cylindrical section 246 can be provided with the catheter body 34 in one piece. A side window 250 is provided between the proximal cylindrical section 246 and the tapered distal section 248, and through which a portion of the annular coring blade 234 extends to cut occluding material. The cutter housing 242 does not rotate together with the cutter 230. In use, the cutter 230 is rotated and dislodged occluding material is received through side window 250 to be transported through the flute defined by the helical turn 240 of the cylindrical shaft 232 and the helical turns of the outer coil 60. A bearing assembly 251 is also preferably provided at the interface between the distal end 72 of the torque member 52 and the distal tapered section 248 of the cutter housing 242.

FIG. 9C illustrates a rotary cutter 260 that can be used to remove a small amount of occluding material. The rotary cutter 260 has a cylindrical shaft 262 with a spherical rotary burr 264 provided at the distal end. The burr 264 has a plurality of circumferential fluted blades 266 provided on the surface of the burr 264 for dislodging occluding material. The cutter 260 is connected to the inner coil 56 of the torque member 52 by sliding the distal end 72 of the inner coil 56 through the hollow lumen of the cylindrical shaft 262, and securing the proximal end 268 of the cylindrical shaft 262 to the distal ends 86 and 88 of the middle and outer coils 58 and 60, respectively. The cutter 260 is provided in, and extends through, a circumferential side window 276 of a two-part cutter housing. The cutter housing has a proximal cylindrical section 272 which is affixed to the distal end 38 of the catheter body 34 by hose-barbed connection, adhesive bonding or other similar affixation means, and a tapered distal section 274 which is affixed to the distal end 72 of the torque member 52 by welding, soldering or other similar affixation means. In use, the distal tapered section 274 rotates together with the burr 264, and dislodged occluding material can be either aspirated through the use of the "screw-pump", or allowed to escape through the patient's blood flow since only a small amount of occluding material is being dislodged and removed. A bearing assembly, such as bearing assembly 100, described above, is also preferably provided at the connection between the catheter body 34 and the rotary cutter 260. In the embodiment illustrated in FIG. 9C, the proximal cylindrical section 272 can actually be part of the shell 104 of the bearing assembly 100.

FIG. 9D illustrates a sidecutter 290 that can be used to remove occluding material. The sidecutter 290 is provided in the form of a distal housing 292 for the distal end 72 of the torque member 52. The distal housing 292 has a tapered cylindrical body having a proximal cylindrical section 294 and a tapered distal section 296 which is affixed to the distal end 72 of the torque member 52 by welding, soldering or other similar affixation means. A side window 298 is provided at one side of the distal end 300 of the distal housing 292. The side window 298 defines a tapered cutting edge 302, and a lateral cutting edge 304. In use, the distal housing 292 rotates together with the torque member 52, with the cutting edges 302 and 304 operating to dislodge occluding material. The occluding material is received through side window 298 to be transported along the flutes defined by the helical turns of the outer coil 60. A bearing assembly, similar to bearing assembly 100 described above, can also be provided at the interface between the proximal cylindrical section 294 and the distal section 38 of the catheter body 34.

During use of the cutters 260 and 290 described hereinabove, the cutters 260 and 290, and their housings 274 and 292 are rotated together with the torque member 52 to dislodge occluding material. However, during the rotation of the cutter 230, its housing 242 is not rotated.

6. A First Method of Use

FIGS. 10A–10M illustrate one method of using the system 30 of the present invention, including certain alternatives and variations.

Figure 10D:
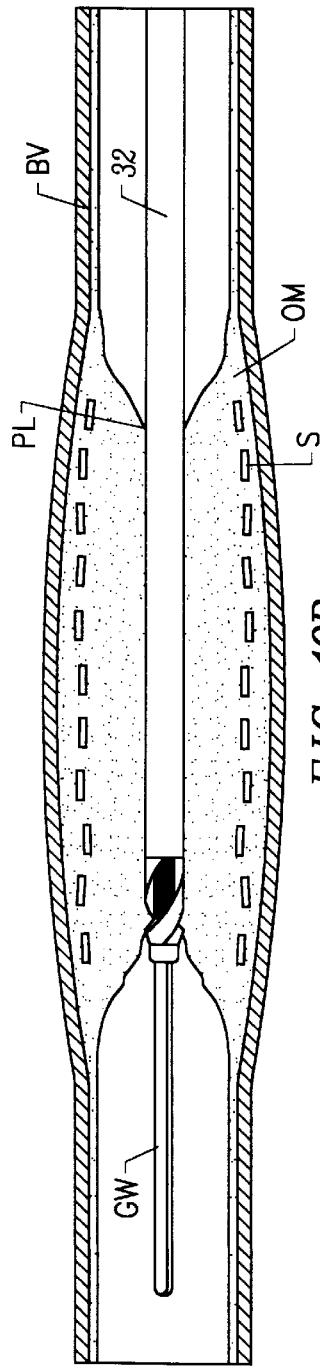
Figure 10E:
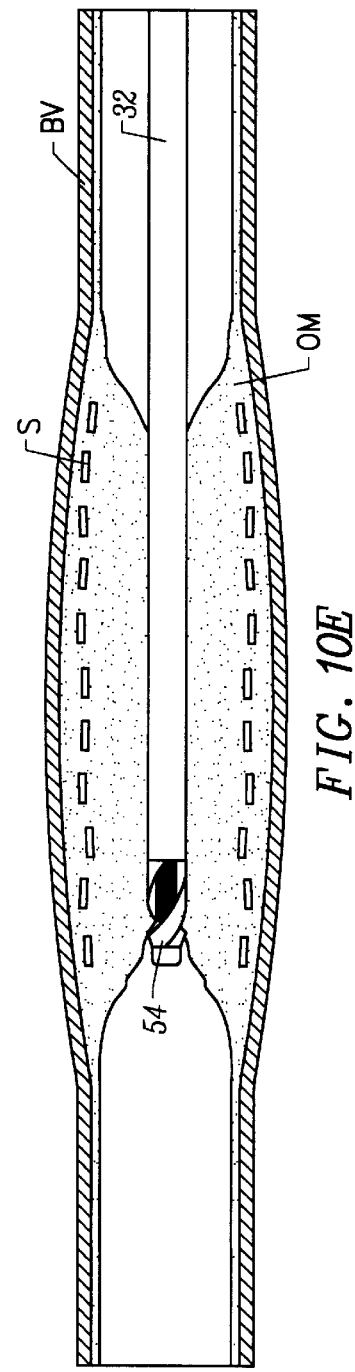

FIG. 10A illustrates a segment of a blood vessel BV that has been partially occluded by occluding material OM at the region where a stent S had previously been implanted. A small occlusion passageway OP is defined between the occluding material OM, and has a diameter which is significantly smaller than the luminal passageway LP of the blood vessel BV. Although FIGS. 10A–10M illustrate the use of the system 30 in connection with a blood vessel BV that has been partially occluded by occluding material OM at the region where a stent S had previously been implanted, the system 30 can also be used with a non-stented blood vessel BV that has been partially occluded (i.e., stenosed) by occluding material OM. The system 30 can also be used in a completely occluded blood vessel, if an initial pilot guidewire, such as the guidewire GW described below, can be passed through the occlusion.

a. First Step—Introduction of Guidewire

In the first step illustrated in FIG. 10B, a straight guidewire GW is percutaneously introduced into the luminal passageway LP using conventional guidewire introduction techniques, and traverses the occluding material OM through the occlusion passageway OP. As part of the conventional guidewire introduction techniques, a guide catheter (not shown) is first introduced into the patient's vasculature through a puncture wound, and the guidewire GW and catheter 32 are subsequently introduced through the lumen of the guide catheter. The guidewire GW can be a conventional stainless steel guidewire. Alternatively, the guidewire GW can be a NiTi guidewire 46 according to the present invention that has been mechanically deformed from its original helical configuration to a generally straight configuration, and which requires thermal inducement to recover its original helical configuration (i.e., does not include a NiTi guidewire operating in superelastic mode). At this time, the physician will assess the location and dimensional characteristics of the occluded segment of the blood vessel BV using conventional angiographic techniques. If a stent S has been implanted adjacent the occluded segment of the blood vessel BV, the length and deployed diameter of the stent S will also be assessed.

b. Second Step—Formation Of Initial Pilot Lumen

After the guidewire GW has been positioned inside and extended through the occlusion passageway OP, the catheter 32 is advanced along the guidewire GW in an "over-the-wire" manner inside the luminal passageway LP to the proximal extent of the occluding material OM. See FIG. 10C. The hand-held device 42 is actuated to cause the removal mechanism 54 to rotate to separate, remove and extract portions of the occluding material OM in the path of the removal mechanism 54 as it is advanced through the occluding material OM. As the catheter 32 is advanced distally over the guidewire GW, the catheter body 34 is not rotated during the rotation of the removal mechanism 54, but will "self-center" itself over the guidewire GW, which has a generally straight configuration within the occluding material OM. When the removal mechanism 54 has reached the distal extent of the occluding material OM, as shown in FIG. 10D, an initial pilot lumen PL will have been formed. This pilot lumen PL will have a diameter which is about the same as the outer diameter or outer dimension of the removal mechanism 54.

c. Third Step—Removal of Guidewire GW

With the initial pilot lumen PL formed in the occluding material OM, the axial position of the catheter 32 is maintained at the distal extent of the occluding material OM and the guidewire GW is removed. See FIG. 10E. The removal of the guidewire GW in this step can be omitted if the guidewire GW is a NiTi guidewire 46 according to the present invention that has been mechanically deformed from its original helical configuration to a generally straight configuration, and which requires thermal inducement to recover its original helical configuration.

d. Fourth Step—Introduction of Guidewire 46

A guidewire 46 according to the present invention is now chosen by the physician. The guidewire 46 can be a superelastic guidewire or a constrained recovery NiTi guidewire. The maximum helical diameter of the helical guide section 200 is chosen to be greater than or equal to the diameter of the pilot lumen PL. The guidewire 46 is also chosen so that the length HL of the helical guide section 200 is greater than or equal to the length of the occluding material OM and the implanted stent S, if applicable. Additionally, the helical guide section 200 is deformed from its original helical configuration to a generally straight configuration so that the subsequent front-loading operation is not impeded by the resistance encountered while advancing the helical guide section 200 through the guidewire lumen 62 in the inner coil 56 of the torque member 52. The deformation is accomplished by elastically deforming the helical guide section 200 without plastically deforming it. If the guidewire is a superelastic guidewire, this deformation is accomplished by front loading the guidewire 46 through the guidewire lumen 62. If the guidewire 46 is a constrained recovery NiTi guidewire, this deformation can be accomplished by, for example, applying sufficient tension to the helical guide section 200 and drawing it through a makeshift die created by a user's thumb and forefinger which simultaneously apply a compressive force to straighten the helical guide section 200. In other words, the twinned martensite which is similar in shape to the parent austenite (i.e., helical) is converted into a deformed martensite which is generally straight.

Figure 10F:
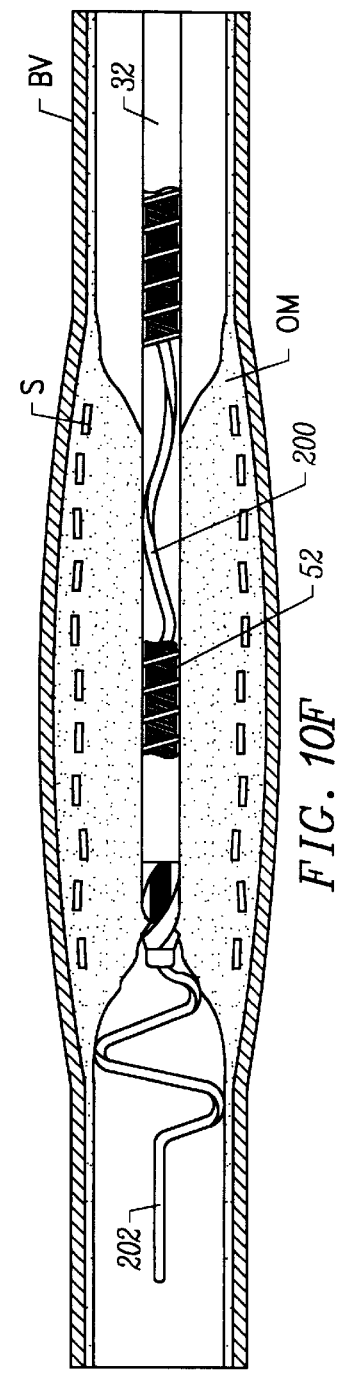

The selected guidewire 46 is then front-loaded into the proximal end 40 of the catheter 32 and advanced until the straight distal end 202 exits from the distal end 72 of the torque member 52. See FIG. 10F. This front-loading step can also be omitted if the initial pilot guidewire GW is a NiTi guidewire 46 according to the present invention that has been mechanically deformed from its original helical configuration to a generally straight configuration, and which requires thermal inducement to recover its original helical configuration. During the front-loading step, the helical guide section 200 is generally straightened-out inside the guidewire lumen 62, as shown in FIG. 10F. Although the helical guide section 200 is not entirely straight when it extends inside the torque member 52, its pitch is significantly looser, and its diameter is significantly smaller, inside the torque member 52 than when it is deployed for use inside the blood vessel BV while lying outside the torque member 52.

e. Fifth Step—Retraction of Catheter 32

The catheter 32 is now retracted until its distal end 38 is at the proximal extent of the occluding material OM. See FIG. 10G. At this time, if the guidewire 46 is a superelastic guidewire, the helical guide section 200 will have naturally assumed its maximum helical configuration, as constrained by the luminal wall of the pilot lumen PL. If the guidewire 46 is a constrained recovery NiTi guidewire, the helical guide section 200 is then heated above its austenite finish temperature $A_f$ so that it returns to its helical shape and diameter as constrained by the pilot lumen PL. The heating can be accomplished by bathing the helical guide section 200 in a physiologically inert fluid (e.g., saline, Ringer's Solution, etc.) that is introduced via the lumen of the guide catheter, or by passing current through the guidewire 46 from its proximal end 204 according to one of the techniques described above.

In either case, the helical guide section 200 now assumes a helical diameter which is defined by the diameter of the pilot lumen PL, in which the helical turns of the helical guide section 200 will be adjacent to, or abut, the occluding material OM. Thus, as shown in FIG. 10G, the helical guide section 200 adapts to the diameter of the pilot lumen PL and the nature (e.g., configuration) of the occluding material OM by positioning its helical turns adjacent to, or abutting, the occluding material OM.

f. Sixth Step—First Pass of Removal Mechanism 54

The distal end 38 of the catheter 32, and the removal mechanism 54, are now advanced over the helical guide section 200. The removal mechanism 54 is rotated during the advancement of the catheter 32 while the guidewire 46 is maintained at the same axial position in the luminal passageway LP. The helical guide section 200 guides the removal mechanism 54 along a helical path that will cause the removal mechanism 54 to engage the occluding material OM. Referring to FIG. 10H, the ability of the helical guide section 200 to conform to the dimensions and nature of the pilot lumen PL and the occluding material OM positions and maintains the removal mechanism 54 in apposition with the luminal wall of pilot lumen PL. Therefore, the removal mechanism 54 is held off-axis with respect to the pilot lumen PL, and at any given axial position within a single wavelength along the helical guide section 200, the removal mechanism 54 is not coplanar with any previous or subsequent axial position along the helical guide section 200. In addition, the pitch of the helical guide section 200 will be looser, and the diameter of the helical guide section 200 will be smaller since the diameter of the pilot lumen PL constrains the guidewire GW and is relatively small compared to the subsequent lumens that are to be created.

The removal mechanism 54 follows the helical path of the helical guide section 200 as it is guided therealong. However, the portions of the helical guide section 200 that are proximal to the removal mechanism 54 become straightened, as best illustrated in FIG. 10H. When the distal end 38 of the catheter 32 reaches the distal-most extent of the occluding material OM, a helical channel HC of occluding material OM will have been removed. See FIG. 10I.

g. Seventh Step—Retract the Removal Mechanism 54 and Axially Translate the Guidewire 46

At this point, the catheter 32 and its removal mechanism 54 are retracted proximally, while the guidewire 46 is maintained at the same axial position in the luminal passageway LP, until the distal end 38 of the catheter 32 is proximal to the occluding material OM. At this time, the helical guide section 200 will again conform itself to the dimension and nature of the existing lumen (which now has one helical channel cut into the occluding material OM and the occluding material.

The guidewire 46 is then repositioned by retracting or advancing it axially by a distance approximate to the width of the helical channel HC, which is equivalent to the axial length of the shearing or cutting aspect of the removal mechanism 54 defined by the proximal cutting edges 76. Again, the helical guide section 200 will conform itself to the dimension and nature of the existing lumen and the occluding material with respect to its new axial position inside the lumen. See FIG. 10J.

h. Eighth Step—Subsequent Passes of Removal Mechanism 54 To Create a Larger Occlusion Passageway OP The removal mechanism 54 is now rotatably advanced again over the helical guide section 200 according to the manner described in the Sixth Step above, to cut another helical channel HC that is confluent with the previously-removed helical channel HC. See FIG. 10K. The seventh and eighth steps are continually repeated until all the removed helical channel HC coalesce and create a larger occlusion passageway OP whose diameter is approximately the same as the maximum helical diameter of the helical guide section 200.

i. Ninth Step—Create One or More Larger Occlusion Passageways OP

If necessary, it is possible to create one or more progressively-larger occlusion passageways. If the existing guidewire 46 is a superelastic guidewire or a constrained NiTi guidewire (without proportional control), then this existing guidewire 46 may be exchanged for another guidewire 46 having a larger-diameter helical guide section 200. The larger-diameter helical guide section 200 of the new guidewire 46 will conform itself to the dimension and nature of the existing lumen OP (which now has a greater diameter than the pilot lumen PL) and the occluding material OM. Again, the ability of the helical guide section 200 to conform to the dimensions and nature of the occlusion passageway OP and the occluding material OM positions and maintains the removal mechanism 54 in apposition with the luminal wall of occlusion passageway OP. The third through eighth steps described above may be repeated to create a larger occlusion passageway OP. See FIG. 10L.

Subsequent guidewires 46 having larger-diameter helical guide sections 200 can be exchanged, and the third through eighth steps described above may be repeated to create increasingly larger occlusion passageways OP, until it is determined that a sufficiently large treated passageway TP has been created. See FIG. 10M. As part of this determination, the physician will consider achieving a treated passageway TP size that is approximately equal to the size of the luminal passageway LP, as well as the relative position and diameter of an implanted stent S, if applicable. The procedure can now be terminated by withdrawing the catheter 32, the guidewire 46, and the guide catheter.

In carrying out the steps of this method, the system 30 and the described method of the present invention are well-suited to protecting the integrity of any stent S that may be implanted in the treated region of the blood vessel BV. This is due in part to the fact that a guidewire 46 can be selected with a helical guide section 200 that is matched to the inner diameter of the stent S to avoid cutting or damaging the stent S.

The ability of the helical guide section 200 to conform to the dimensions and nature of the luminal passageway LP and the occluding material OM allow the removal mechanism 54 to be used safely with occluding material OM that is not consistent in nature. For example, the forces or stress exerted by the helical guide section 200 on the luminal wall are highest in the most constrained cross-sections (i.e., in the passageways having the smallest diameters). In the immediate areas of the constrained cross-section (or areas with a greater volume of occluding material OM), the removal mechanism 54 is more forcibly directed (by the helical guide section 200) in an outward direction and therefore takes a deeper cut of the occluding material OM. The deeper cut allows that portion of the cross-section to "catch up" with the other less constraining portions (or areas with a smaller volume of occluding material OM) to generally create a neolumen which gradually takes on a more regular and circularly symmetrical shape. As the lumen is enlarged by subsequent passes of the removal mechanism 54, a progressively lesser force will be exerted by the helical guide section 200 against the luminal wall.

7. A Second Method of Use

The method of use illustrated in connection with FIGS. 10A–10M can be modified if the guidewire 46 is a constrained recovery NiTi guidewire with proportional control.

According to this modified method, in the First step, the guidewire GW initially introduced is a constrained recovery NiTi guidewire with proportional control that has already been deformed from its original helical configuration to a generally straight configuration according to the methods disclosed in connection with the Fourth step above. As a result, the Third and Fourth steps are omitted. In the Fifth step, the heat applied to the helical guide section 200 is titrated to cause the helical guide section 200 to re-acquire a helical configuration, but not the maximum helical diameter. Finally, in the Ninth step, instead of exchanging the existing guidewire 46 with other guidewires 46 having progressively larger helical sections 200, the heat applied to the helical guide section 200 is carefully titrated to cause the helical guide section 200 to progressively re-acquire (i.e., in a step-wise manner) its maximum helical configuration. Thus, only one guidewire 46 is needed for the procedure.

Thus, the present invention provides a system 30 and methods that are effective in separating, removing and extracting occluding material from a body lumen. The helical guide section 200 of the guidewire 46 allows the removal mechanism 54 to create a passageway in occluding material OM that is diametrically larger than the dimension of the removal mechanism 54. The provision of the guidewire 46 and its helical guide section 200 also allows the physician to carefully select a helical guide section 200 with the optimum size (or diameter) to avoid injuring the luminal wall of the vessel, or damaging an implanted stent. This ability to select the size of the luminal passageway to be created allows the system 30 and methods of the present invention to be used in a wide variety of applications, patients and conditions. The system 30 and methods of the present invention are also simple to use.

Although the guidewire 46 of the present invention, and its guide section 200, has been described for use with a removal mechanism, it is also possible to use the guidewire 46 and its guide section 200 together with catheters or probes in other applications, such as but not limited to diagnostic (e.g., intravascular ultrasound imaging, angioscopy, fluoroscopy), energy delivery (e.g., laser, cryogenics, radiation, photodynamic therapy, brachytherapy, ultrasound angioplasty), cutting (e.g., directional coronary atherectomy catheters, transluminal extraction catheters), ablation (e.g., rotational atherectomy catheters), thrombectomy, selective biopsy, and drug delivery. In this regard, the guide section 200 can provide effective stabilization for an associated device when used, for example, in angioscopy, ultrasound imaging, and monitoring arteries in critical care applications (e.g., measuring pressure and flow measurements, and oximetry).

Figure 11:
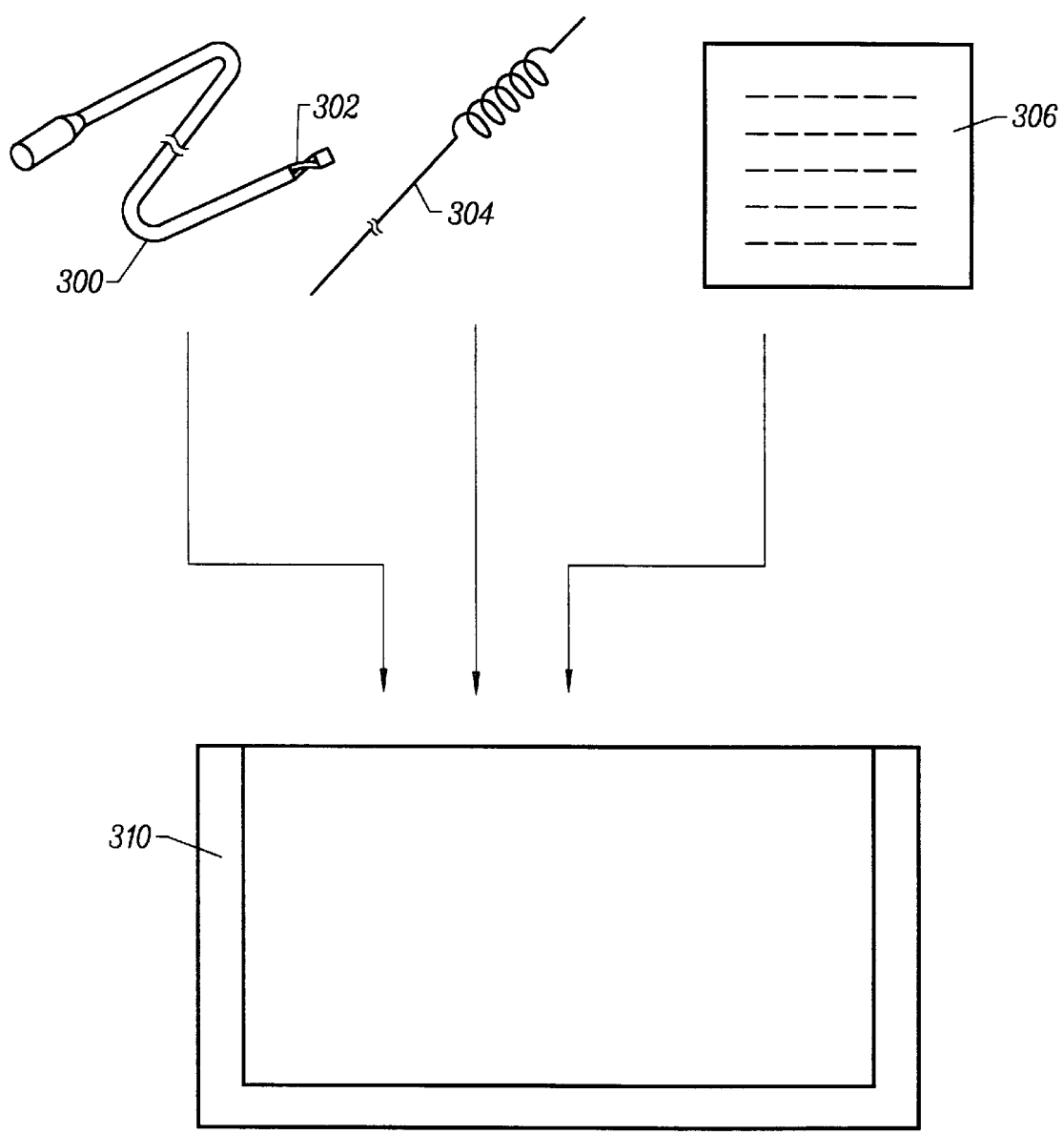
FIG. 11 illustrates a kit according to the present invention.

The present invention further provides kits for performing the methods of the present invention, as illustrated in FIG. 11. The kits comprise catheters 300 having cutting tips 302, guidewires 304 as described above, and instructions for use 306 setting forth the methods for using the catheters in combination with the guidewires. the kit components will usually be packaged together in a conventional package 310, such as a pouch, box, tube, tray, or the like, which will usually be sterilized. The instructions 306 may be in the form of a package insert (as illustrated), or may be printed in whole or in part on the package 310 itself.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method of treating a region of occluding material in a body lumen, comprising:
   a. introducing a guidewire into the body lumen and through the region of occluding material;
   b. introducing a catheter over the guidewire, the catheter having a removal mechanism disposed at its distal end;
   c. creating an initial pilot lumen through the occluding material;
   d. retracting the catheter and removal mechanism to a position along the guidewire that is proximal to the occluding material;
   e. providing a guide section in the guidewire having a curved profile that is diametrically larger than the dimension of the removal mechanism;
   f. advancing the removal mechanism along the guide section to separate occluding material leaving a first curved channel therein;
   g. retracting the catheter and removal mechanism to a position along the guidewire that is proximal to the occluding material;
   h. axially translating the guide section of the guidewire within the occluding material; and
   i. advancing the removal mechanism along the guide section to separate and remove a second curved channel in the occluding material that is confluent with the first curved channel in the occluding material.

2. The method of claim 1, further including the steps of:
   j. retracting the catheter and removal mechanism to a position along the guidewire that is proximal to the occluding material;
   k. axially translating the guide section of the guidewire within the occluding material;
   l. advancing the removal mechanism along the guide section to separate and remove a third curved channel in the occluding material that is confluent with the first and second curved channels in occluding material; and
   m. repeating steps (j) through (l) until all confluent channels in the occluding material have been removed to create a new larger-diameter luminal passageway.

3. The method of claim 1, further including the steps of:
   j. retracting the catheter and removal mechanism to a position along the guidewire that is proximal to the occluding material;
   k. increasing the dimension of the guide section of the guidewire; and
   l. advancing the removal mechanism along the guide section to separate and remove a third curved channel of occluding material which has a larger diameter than the first curved channel in the occluding material.

4. The method of claim 3, wherein step (k) includes the step of applying heat to the guide section of the guidewire.

5. The method of claim 1, further including the steps of:
   j. advancing the catheter and removal mechanism to a position along the guidewire that is distal to the occluding material;
   k. exchanging the guidewire with a second guidewire having a guide section with a larger dimension than the guide section of the removed guidewire;
   l. retracting the catheter and removal mechanism to a position along the guidewire that is proximal to the occluding material; and
   m. advancing the removal mechanism along the guide section of the second guidewire to separate and remove a third curved channel in the occluding material which has a larger diameter than the first curved channel in the occluding material.

6. The method of claim 1, wherein step (e) includes the step of providing the guide section with a helical configuration.

7. The method of claim 6, wherein step (e) further includes the step of providing the guide section of the guidewire in the form of a nickel-titanium alloy.

8. The method of claim 1, wherein step (e) further includes the step of causing the guide section to exert a radially outward force against the pilot lumen.

9. The method of claim 1, wherein step (e) further includes the step of providing the guide section from a shape memory material having sufficient flexibility to assume a generally straightened configuration when the guide section extends through a lumen of a torque member.

10. The method of claim 1, wherein step (e) further includes the step of providing the guide section from a material that remains in its elastic state when the guide section extends through a lumen of a torque member.

11. A method of treating a region of occluding material in a body lumen, comprising the steps of:
   a. introducing a first guidewire into the body lumen and through the region of occluding material;
   b. introducing a catheter over the first guidewire, the catheter having a removal mechanism disposed at its distal end;
   c. creating an initial pilot lumen through the occluding material;
   d. removing the first guidewire;
   e. introducing a second guidewire through a lumen of the catheter, the second guidewire having a guide section with a curved profile that is diametrically larger than the dimension of the removal mechanism;
   f. retracting the catheter and removal mechanism to a position along the second guidewire that is proximal to the occluding material;
   g. advancing the removal mechanism along the guide section to separate and remove a first curved channel in the occluding material;
   h. retracting the catheter and removal mechanism to a position along the second guidewire that is proximal to the occluding material;
   i. axially translating the guide section of the second guidewire within the occluding material; and
   j. advancing the removal mechanism along the guide section to separate and remove a second curved channel in the occluding material that is confluent with the first curved channel in the occluding material.

12. The method of claim 11, further including the steps of:
   k. axially translating the guide section of the second guidewire within the occluding material; and
   l. advancing the removal mechanism along the guide section to separate and remove a third curved channel in the occluding material that is confluent with the first and second curved channels in the occluding material.

13. The method of claim 11, further including the steps of:
   k. retracting the catheter and removal mechanism to a position along the second guidewire that is proximal to the occluding material;
   l. increasing the dimension of the guide section of the second guidewire; and m. advancing the removal mechanism along the guide section to separate and remove a third curved channel in the occluding material which has a larger diameter than the first curved channel in the occluding material.

14. The method of claim 13, wherein step (l) includes the step of applying heat to the guide section of the second guidewire.

15. The method of claim 11, further including the steps of:
k. retracting the catheter and removal mechanism to a position along the second guidewire that is proximal to the occluding material;
l. exchanging the second guidewire with a third guidewire having a guide section with a larger dimension than the guide section of the second guidewire; and
m. advancing the removal mechanism along the guide section of the third guidewire to separate and remove a third curved channel of occluding material which has a larger diameter than the first curved channel of occluding material.

16. The method of claim 11, wherein step (e) includes the step of providing the guide section with a helical configuration.

17. The method of claim 16, wherein step (e) further includes the step of providing the guide section of the second guidewire in the form of a superelastic material.

18. The method of claim 11, wherein step (e) further includes the step of providing the guide section of the second guidewire in the form of a nickel-titanium alloy.

19. The method of claim 11, wherein step (f) further includes the step of causing the guide section to exert a radially outward force against the pilot lumen.

20. The method of claim 11, wherein step (e) further includes the step of providing the guide section from a shape memory material having sufficient flexibility to assume a generally straightened configuration when the guide section extends through a lumen of a torque member.

21. The method of claim 11, wherein step (e) further includes the step of providing the guide section from a material that remains in its elastic state when the guide section extends through a lumen of a torque member.

22. A method of treating a region of occluding material in a body lumen, comprising the steps of:
a. creating an initial pilot lumen through the occluding material;
b. introducing into the pilot lumen a guide mechanism having a curved profile which positions portions of the guide mechanism adjacent the occluding material; and
c. advancing a removal mechanism along the guide mechanism to separate and remove a first plurality of generally confluent curved channels to form a first passageway through the occluding material which is diametrically larger than the pilot lumen.

23. The method of claim 22, further including the step of:
d. further advancing the removal mechanism along the guide mechanism to separate and remove a second plurality of generally confluent curved channels to form a second passageway through the occluding material which is diametrically larger than the first passageway.

24. The method of claim 23, wherein step (d) further includes the step of:
d1. increasing the dimension of the curved profile of the guide mechanism to position portions of the guide mechanism adjacent the occluding material.

25. The method of claim 22, wherein step (c) further includes the step of:
c1. advancing the removal mechanism along the guide mechanism to separate and remove a first curved channel;
c2. axially translating the guide mechanism within the pilot lumen; and
c3. advancing the removal mechanism along the guide mechanism to separate and remove a second curved channel which is confluent with the first curved channel.

26. The method of claim 22, wherein step (b) further includes the step of providing the curved profile with a helical configuration.

27. The method of claim 22, wherein step (b) further includes the step of causing the guide mechanism to exert a radially outward force against the pilot lumen.

28. The method of claim 22, wherein step (b) further includes the step of providing the guide mechanism from a shape memory material having sufficient flexibility to assume a generally straightened configuration when the guide mechanism extends through a lumen of a torque member.

29. The method of claim 22, wherein step (e) further includes the step of providing the guide mechanism from a material that remains in its elastic state when the guide mechanism extends through a lumen of a torque member.

* * * * *